(12) United States Patent
Tan

(10) Patent No.: US 9,457,151 B2
(45) Date of Patent: Oct. 4, 2016

(54) NEEDLELESS DRUG-INJECTING SYSTEM AND METHOD THEREOF

(71) Applicant: Gold NanoTech Inc, Taipei (TW)

(72) Inventor: Shan-Wen Tan, Taipei (TW)

(73) Assignee: GOLD NANOTECH INC. (TW)

( * ) Notice: Subject to any disclaimer, the term of this patent is extended or adjusted under 35 U.S.C. 154(b) by 331 days.

(21) Appl. No.: 14/150,920

(22) Filed: Jan. 9, 2014

(65) Prior Publication Data

US 2015/0051574 A1 Feb. 19, 2015

(30) Foreign Application Priority Data

Aug. 16, 2013 (TW) .............................. 102129488 A

(51) Int. Cl.
| | |
|---|---|
| *A61M 39/00* | (2006.01) |
| *A61M 5/30* | (2006.01) |
| *A61M 5/20* | (2006.01) |
| *A61M 5/31* | (2006.01) |

(52) U.S. Cl.
CPC ......... *A61M 5/3007* (2013.01); *A61M 5/2053* (2013.01); *A61M 5/30* (2013.01); *A61M 2005/3128* (2013.01); *A61M 2005/3142* (2013.01)

(58) Field of Classification Search
CPC ....... A61M 5/30; A61M 39/10; A61M 5/204
See application file for complete search history.

(56) References Cited

U.S. PATENT DOCUMENTS

| | | | | |
|---|---|---|---|---|
| 4,421,508 A | * | 12/1983 | Cohen ............................ | 604/70 |
| 4,666,430 A | * | 5/1987 | Brown et al. ................. | 604/141 |
| 5,746,714 A | * | 5/1998 | Salo et al. ...................... | 604/68 |
| 5,911,703 A | * | 6/1999 | Slate et al. ..................... | 604/68 |
| 5,993,412 A | * | 11/1999 | Deily et al. .................... | 604/68 |
| 6,669,664 B2 | * | 12/2003 | Slate et al. ..................... | 604/68 |
| 9,211,377 B2 | * | 12/2015 | DiPerna et al. | |

* cited by examiner

*Primary Examiner* — Scott Medway

(57) ABSTRACT

The present invention relates to a needleless drug-injecting system and a drug-injecting method thereof, wherein the needleless drug-injecting system comprises a controlling device and a needleless drug-injecting device. By using the needleless drug-injecting system and the drug-injecting method, a user is able to individually set a variety of parameters comprising usage dose of liquid medicine, shot pressure of liquid medicine, air flow rate, single-shot quantity of liquid medicine, continuous shot frequency of liquid medicine, and a continuous shot spacing time according to different liquid medicine. Thus, after setting the parameters, the liquid medicine can be injected into the dermis layer of the face skin of a human when the user using this needleless drug-injecting system to inject any one liquid medicine to the human face, therefore the liquid medicine would be absorbed by the face skin without hurting the human face.

13 Claims, 25 Drawing Sheets

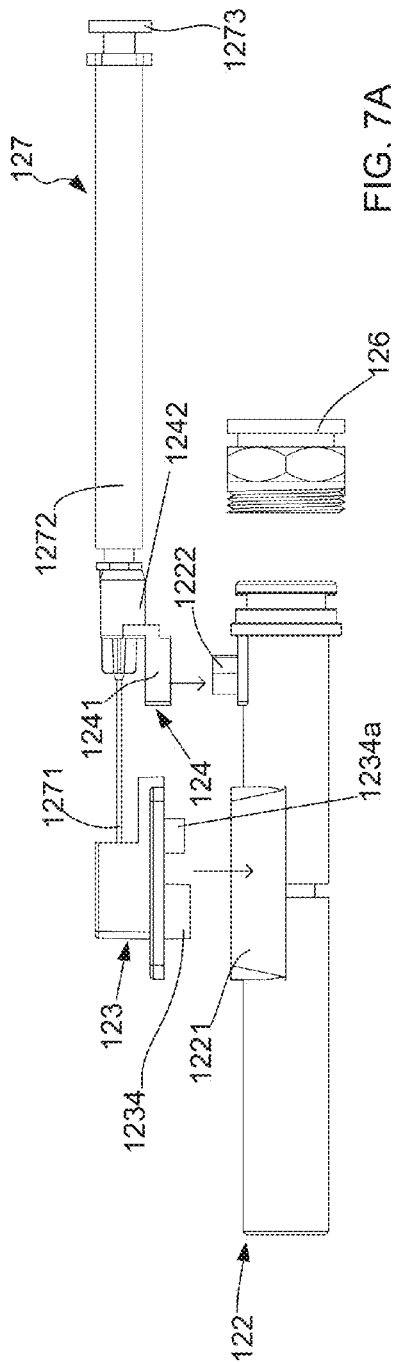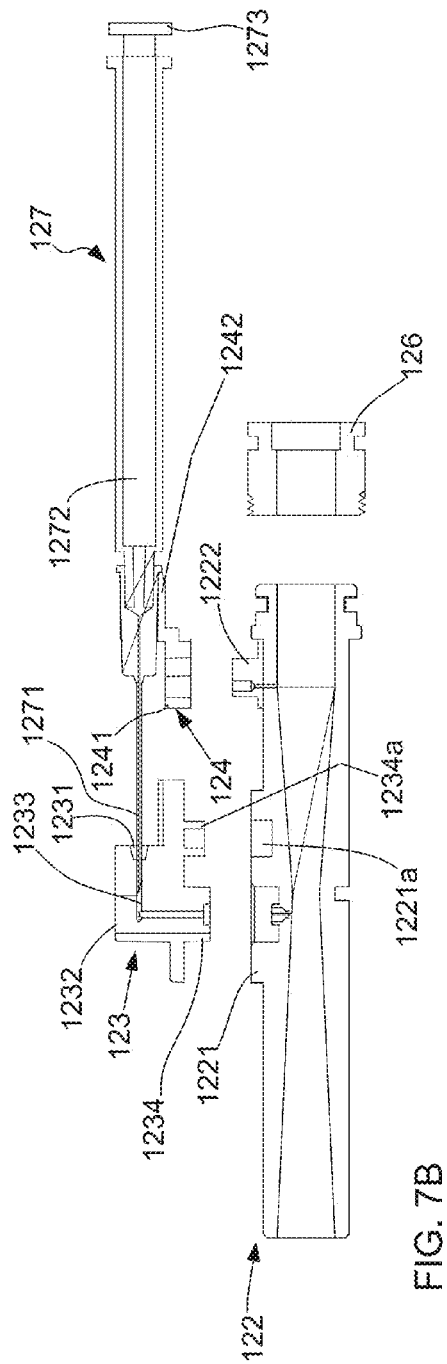

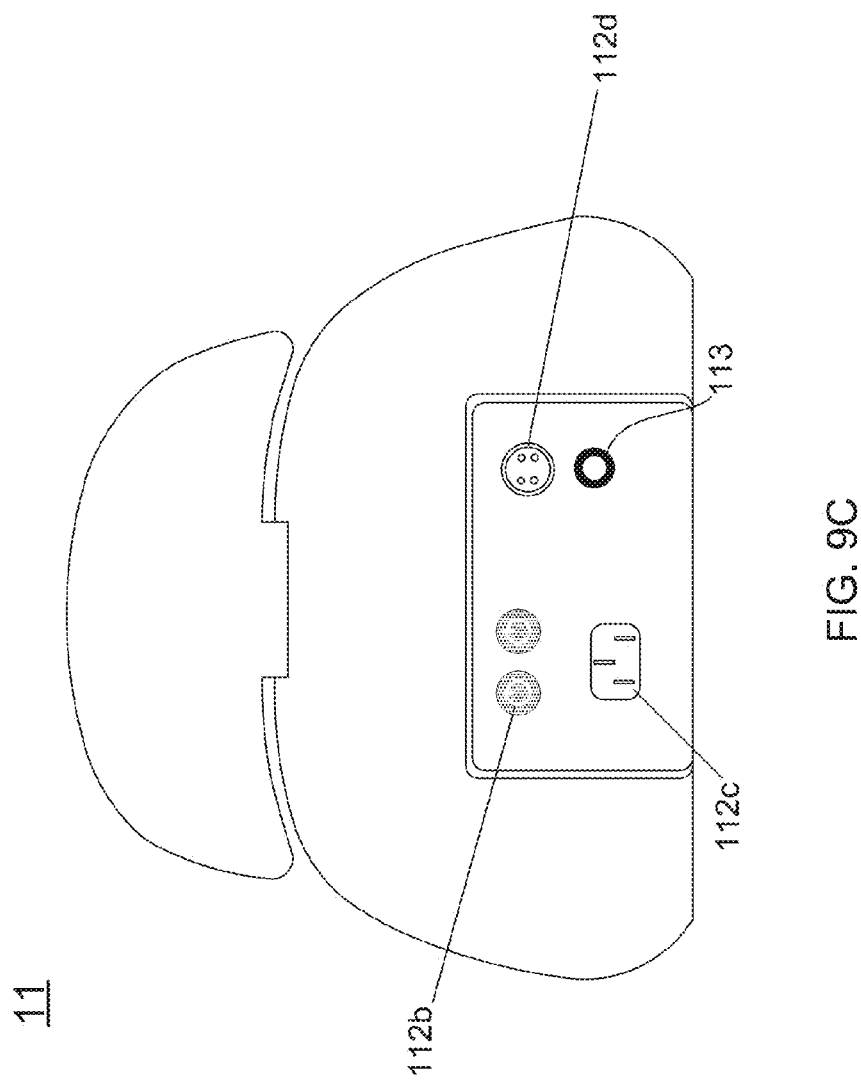

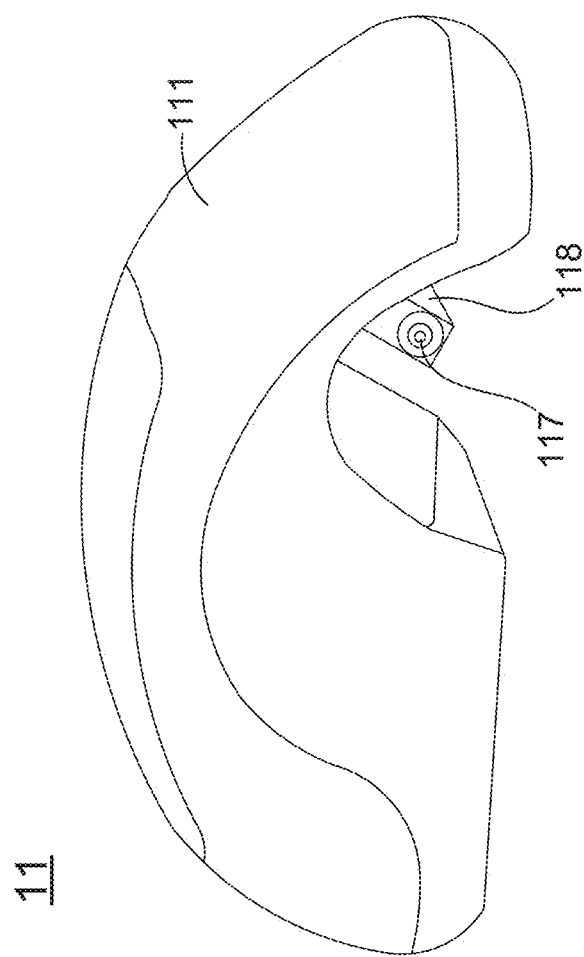

<u>12</u>

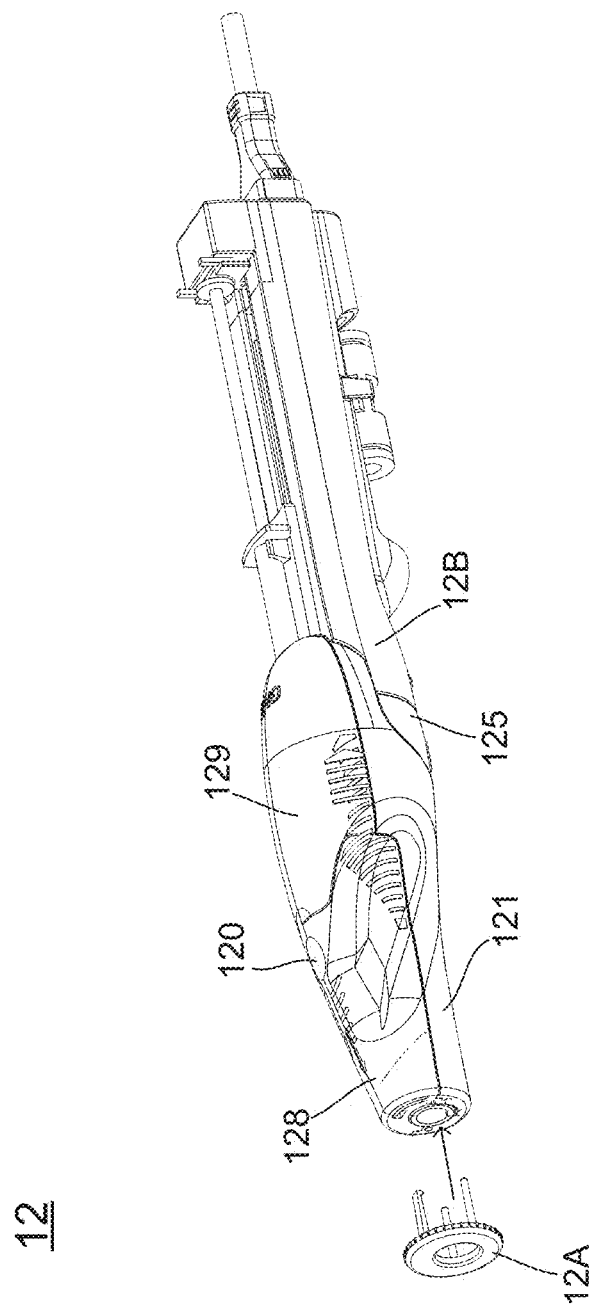

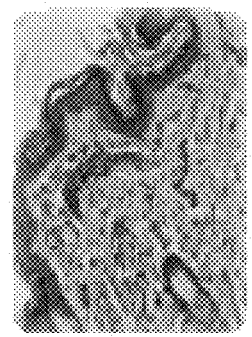
FIG. 12

NEEDLELESS DRUG-INJECTING SYSTEM AND METHOD THEREOF

BACKGROUND OF THE INVENTION

1. Field of the Invention

The present invention relates to a needleless drug-injecting equipment, and more particularly to a needleless drug-injecting system and a drug-injecting method thereof, which a user to set a plurality of specific parameters, wherein the specific parameters comprises: a usage dose of the liquid medicine, a shot pressure of the liquid medicine, an air flow rate, a single-shot quantity of the liquid medicine, a continuous shot frequency of the liquid medicine, and a continuous shot spacing time.

2. Description of the Prior Art

Recently, needleless drug-injecting device has been widely used and its advantages has been confirmed as follows: (1) the needleless drug-injecting device would not hurt human skin and damage skin tissue because of without using any injection needle; and (2) the needleless drug-injecting device would not hurt medical workers because of without using any injection needle.

With reference to FIG. 1 and FIG. 2, which respectively illustrate a stereo view and a side view of a conventional manual needleless drug-injecting device; moreover, please refer to FIG. 3, there is shown a cross-sectional side view of the conventional manual needleless drug-injecting device. As shown in FIG. 1, FIG. 2 and FIG. 3, the conventional manual needleless drug-injecting device 10' consists of: an inner housing 12', an outer housing 28', a skin tensioning spring 30', a vial 18', a nozzle 40', a skin tensioner 43', a ram 44', a trigger 45', a trigger mechanism 32', and an injection delivery spring 36'. The operation procedure of the manual needleless drug-injecting device 10' is as follows:

Step (1) selecting a proper skin tensioning spring 30' and an appropriate injection delivery spring 36';

Step (2) selecting a liquid medicine to be injected in to a human skin 22', and filling the liquid medicine into the vial 18';

Step (3) disposing the vial 18' in the inner housing 12';

Step (4) making the skin tensioner 43' push against to an injection area on the human skin 22'; and Step (5) making the vial 18' produce an injecting flow 34' passing through the nozzle 40' by pressing the trigger mechanism 32', and then the injecting flow impacts injection area on the human skin 22'.

Thus, through above descriptions, it is able to know that the manual needleless drug-injecting device 10' includes the advantages of:

1. The manual needleless drug-injecting device 10' provides the users to complete a liquid medicine injection, without using any pressured air source;
2. Through the skin tensioner 43', the manual needleless drug-injecting device 10' is able to easily inject the liquid medicine in to human skin after the human skin is tensioned by the skin tensioner 43'.

However, in spite of the manual needleless drug-injecting device 10' includes many advantages, the manual needleless drug-injecting device 10' still includes some drawbacks and shortcomings of:

A. The manual needleless drug-injecting device 10' can using different skin tensioning springs 30' and injection delivery springs 36' to carry out the liquid medicine injection according to different human skin 22', but cannot be set with different injection pressure according to different molecular weights of the drug fluids.

B. The fluid injection carries out by the manual needleless drug-injecting device 10' is driven by the skin tensioning spring 30'; for this reason, it can assume that the manual needleless drug-injecting device 10' can merely complete the fluid injection by on single shot, but cannot achieve multi shot of the fluid injection during a specific drug-shooting interval.

C. Inheriting to above point B, it can also understand that the manual needleless drug-injecting device 10' cannot be set with the one single-shot quantity of liquid medicine.

Accordingly, in view of the conventional manual needleless drug-injecting device 10' still includes drawbacks and shortcomings, the inventor of the present application has made great efforts to make inventive research thereon and eventually provided a needleless drug-injecting system and a drug-injecting method by using the same.

SUMMARY OF THE INVENTION

The primary objective of the present invention is to provide a needleless drug-injecting system and a drug-injecting method thereof, wherein the needleless drug-injecting system comprises a controlling device and a needleless drug-injecting device. By using the needleless drug-injecting system and the drug-injecting method, a user is able to individually set a variety of parameters comprising usage dose of liquid medicine, shot pressure of liquid medicine, air flow rate, single-shot quantity of liquid medicine, continuous shot frequency of liquid medicine, and a continuous shot spacing time according to different liquid medicine. Thus, after setting the parameters, the liquid medicine can be injected into the dermis layer of the face skin of a human when the user using this needleless drug-injecting system to inject any one liquid medicine to the human face, therefore the liquid medicine would be absorbed by the face skin without hurting the human face.

Accordingly, to achieve the primary objective of the present invention, the inventor of the present invention provides a needleless drug-injecting system, comprising:

a needleless drug-injecting device, having a first base;

a liquid medicine delivering tube, disposed in the first base and respectively formed with an air input end and a liquid medicine output end on the two ends thereof, wherein one side of the liquid medicine delivering tube is provided with an delivery member combining portion;

a liquid medicine delivery member, disposed on the liquid medicine delivering tube and having an insertion hole and a pressure relieving hole;

a fixed connection base, connected to the rear end of the first base and having a sleeve tube, wherein the front of the sleeve tube is connected the air input end of the liquid medicine delivering tube;

a tube connecting member, connected with the rear end of the sleeve tube of the fixed connection base;

an injection syringe, having a needle, a barrel and a plunger, wherein the needle of the injection syringe is inserted into the insertion hole of the liquid medicine delivery member;

a sliding cover set, assembled with the first base for constituting a housing, wherein the liquid medicine delivering tube, the liquid medicine delivery member, and the fixed connection base are accommodated by the housing;

an adjustable nozzle, assembled to a front opening of the housing, wherein a speed-adjusting distance is provided between the adjustable nozzle and the front opening of the housing, and the speed-adjusting distance can be changed by adjusting the distance between the adjustable nozzle and the front opening, so as to modify the speed of a liquid medicine be shot according to the molecular weight of the liquid medicine;

a second base, assembled to the rear end of the first base, and an extension tube and an air delivery tube being connected to the bottom of the second base, wherein the extension tube is further coupled to the air input end of the liquid medicine delivering tube through the tube connecting member and the fixed connection base in the housing;

a driving module, disposed in the second base and having a plunger fixing member for fixing a pressing portion of the plunger, wherein the driving module is controlled by a controlling circuit module, so as to steppedly push the pressing portion and make the liquid medicine stored in the barrel of the injection syringe be quantitatively injected into the liquid medicine delivery member, and then the liquid medicine is delivered into the liquid medicine delivering tube from the liquid medicine delivery member;

a controlling device, electrically connected to the controlling circuit module of the needleless drug-injecting device through an electrical cable thereof, and comprising: a box provided with an air pressure modulating module and a controlling and processing model in the internal thereof;

a first air inputting port, disposed on one side of the box, and used for connecting an external air source, wherein a first air provided by the air source is inputted into the air pressure modulating module through the first air inputting port;

an air pressure adjusting valve, used for modulating the air pressure of the first air;

a solenoid valve controlling output port, disposed on the one side of the box and connected to the air pressure modulating module, used for outputting the first air having a specific air pressure;

an electrical connection port, disposed on one side of the box and coupled to the controlling and processing module, moreover, the electrical connection port being also connected to the electrical cable; and an operation interface, disposed on the front side of the box, and providing a user to set a plurality of specific parameters, wherein the specific parameters comprises: a usage dose of the liquid medicine, a shot pressure of the liquid medicine, an air flow rate, a single-shot quantity of the liquid medicine, a continuous shot frequency of the liquid medicine, and a continuous shot spacing time.

Moreover, to achieve the primary objective of the present invention, the inventor of the present invention provides a needleless drug-injecting method, comprising the steps of:
(1) connecting an extended tube and an air delivery tube to the bottom of a second base of a needleless drug-injecting device of the needleless drug-injecting system, so as to facilitate the extended tube couple with an air input end of a liquid medicine delivering tube disposed in a first base of the needleless drug-injecting device through a tube connecting member and a fixed connection base;
(2) connecting the air delivery tube to a solenoid valve controlling output port of a box of a controlling device of the needleless drug-injecting system;
(3) connecting the two terminals of an electrical cable to a controlling circuit module of the needleless drug-injecting device and an electrical connection port of the box;
(4) connecting an inputting port of the box to an air source for providing the first are or an air providing device for providing a second air of the box, so as to input the first air or the second air into the box;
(5) opening the housing of the needleless drug-injecting device by sliding a sliding cover set thereof;
(6) disposing a new liquid medicine delivering tube provided with one liquid medicine delivery member and one needle fixing member in the first base, where a needle head of a needle of a injection syringe is fixed on the needle fixing member, and the needle head is inserted into an insertion hole of the liquid medicine delivery member;
(7) closing the housing by sliding the sliding cover set;
(8) filling a liquid medicine into a barrel of the injection syringe;
(9) disposing the barrel filled with the liquid medicine and a plunger of the injection syringe on an injection syringe carrying board disposed on the second base, and make the front end of the barrel combined with the needle fixed by the needle fixing member;
(10) disposing a pressing portion of the plunger on a plunger fixing member of a driving module disposed in the second base;
(11) modulating the air pressure of the inputted first air or the inputted second air by using an air pressure modulating module of the box;
(12) setting a plurality of specific parameters consisting of a usage dose of the liquid medicine, a shot pressure of the liquid medicine, an air flow rate, a single-shot quantity of the liquid medicine, a continuous shot frequency of the liquid medicine, and a continuous shot spacing time by using an operation interface of the box according to the molecular weight of the liquid medicine;
(13) changing a speed-adjusting distance provided between an adjustable nozzle and a front opening of the housing by adjusting the distance between the adjustable nozzle and the front opening according to the molecular weight of the liquid medicine;
(14) making the needleless drug-injecting device shoot out the liquid medicine onto a target object through a controlling and processing module and an air pressure modulating module disposed in the box; and
(15) pressing a manual shot-triggering member formed on front end of the bottom of the second base, so as to exhaust the residual first air or the residual second air out of the extended tube through a pressure relieving hole and the front opening of the housing, and then a liquid medicine injection procedure is completed.

BRIEF DESCRIPTION OF THE DRAWINGS

The invention as well as a preferred mode of use and advantages thereof will be best understood by referring to the following detailed description of an illustrative embodiment in conjunction with the accompanying drawings, wherein:

FIG. 7A is a top view of a liquid medicine delivering tube, a needle fixing member, a fixed connection base, a tube connecting member, and an injection syringe of the needleless drug-injecting device;

FIG. 7B is a cross-sectional view of the liquid medicine delivering tube, the needle fixing member, the fixed connection base, the tube connecting member, and the injection syringe of the needleless drug-injecting device;

FIGS. 9A, 9B and 9C are side views of a controlling device of the needleless drug-injecting system;

FIG. 12 is slice images of rat skin tissues; and

DETAILED DESCRIPTION OF THE PREFERRED EMBODIMENTS

To more clearly describe a needleless drug-injecting system and a drug-injecting method by using the same according to the present invention, embodiments of the present invention will be described in detail with reference to the attached drawings hereinafter.

Figure 1:
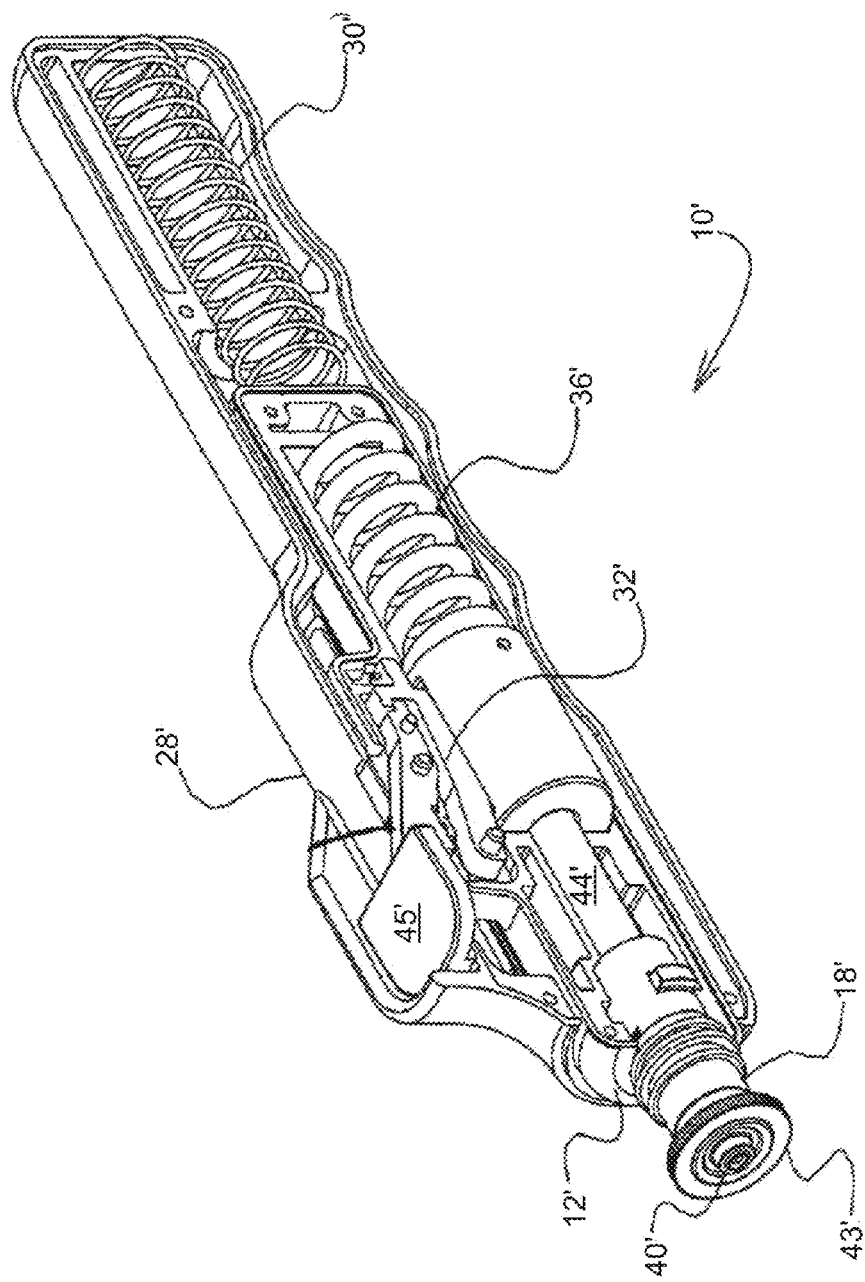
FIG. 1 is a stereo view of a conventional manual needleless drug-injecting device.
Figure 2:
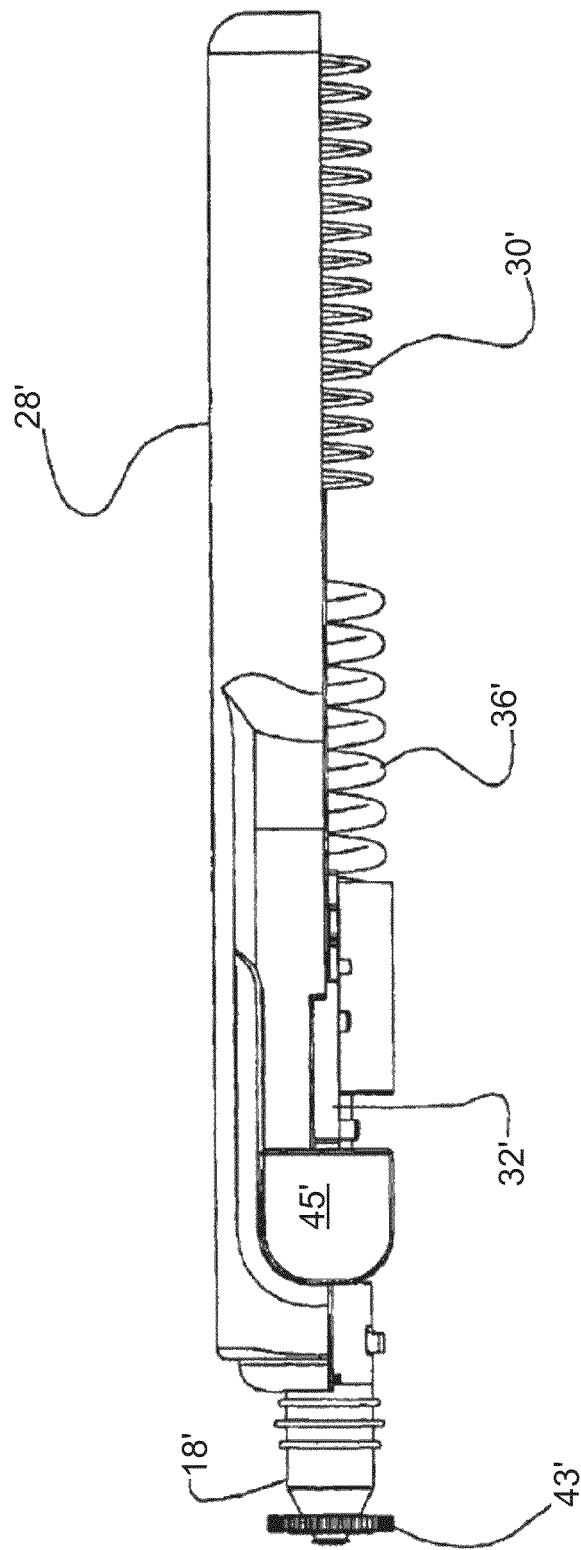
FIG. 2 is a side view of the conventional manual needleless drug-injecting device.
Figure 3:
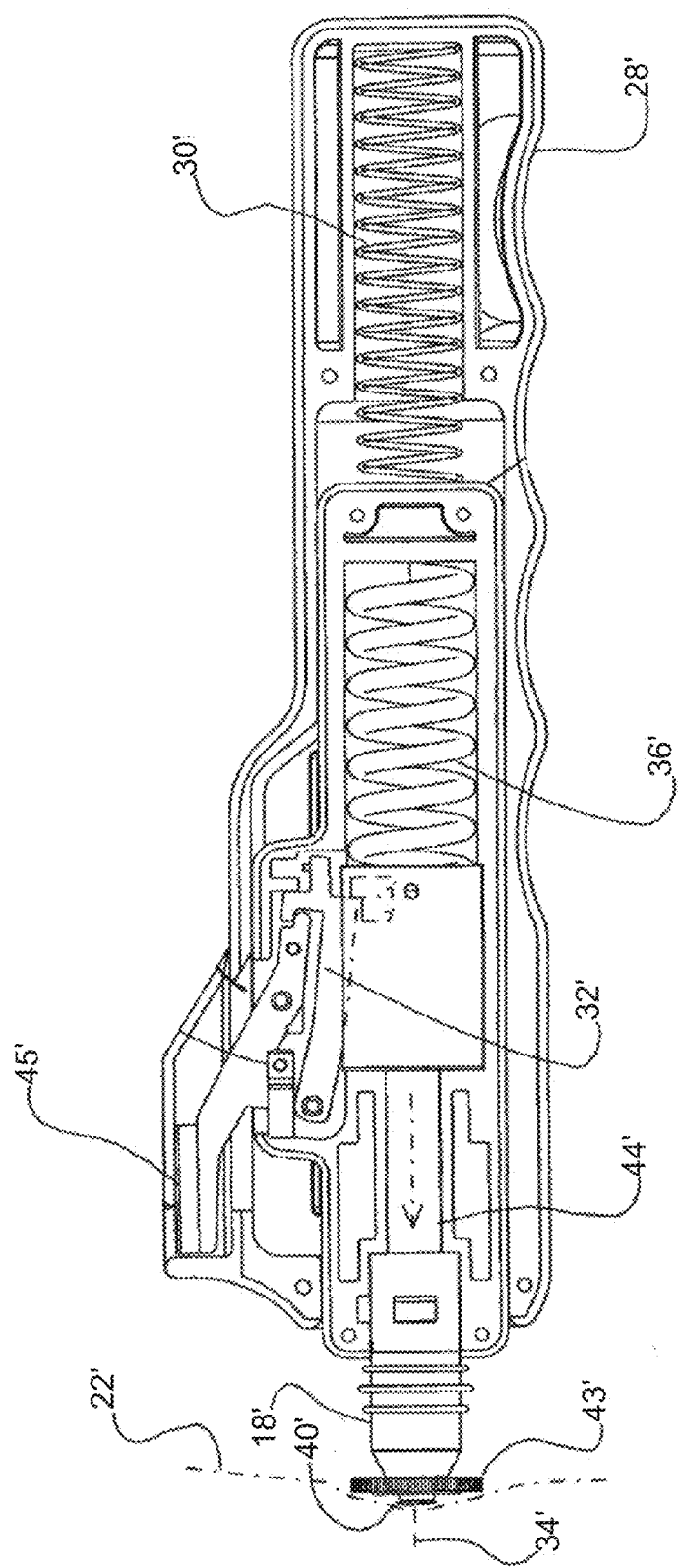
FIG. 3 is a cross-sectional side view of the conventional manual needleless drug-injecting device.
Figure 4:
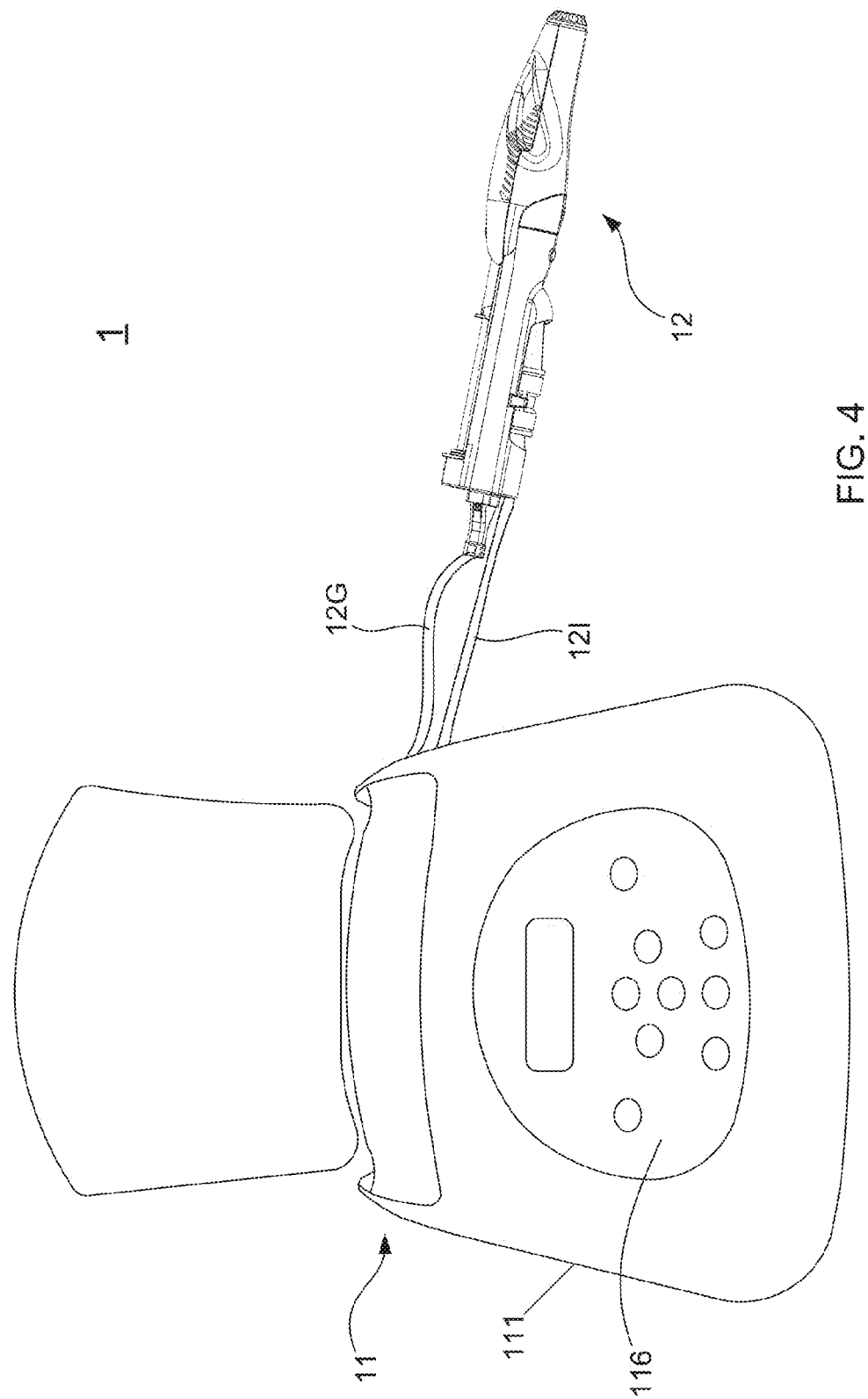
FIG. 4 is a side view of a needleless drug-injecting system according to the present invention.

With reference to FIG. 4, which illustrates a stereo view of a needleless drug-injecting system according to the present invention. As shown in FIG. 4, the needleless drug-injecting system 1 mainly consists of a needleless drug-injecting system device 12 and a controlling device 11. The controlling device 11 is electrically connected to the rear end of the needleless drug-injecting device 12 through an electrical cable 12G; moreover, an air delivery tube 121 of the controlling device 11 is connected to the bottom of the rear end of the needleless drug-injecting system device 12 for inputting an air with a specific air pressure into the needleless drug-injecting system device 12, and then the controlling device 11 can control the needleless drug-injecting system device 12 to shot out a liquid medicine.

Figure 5A:
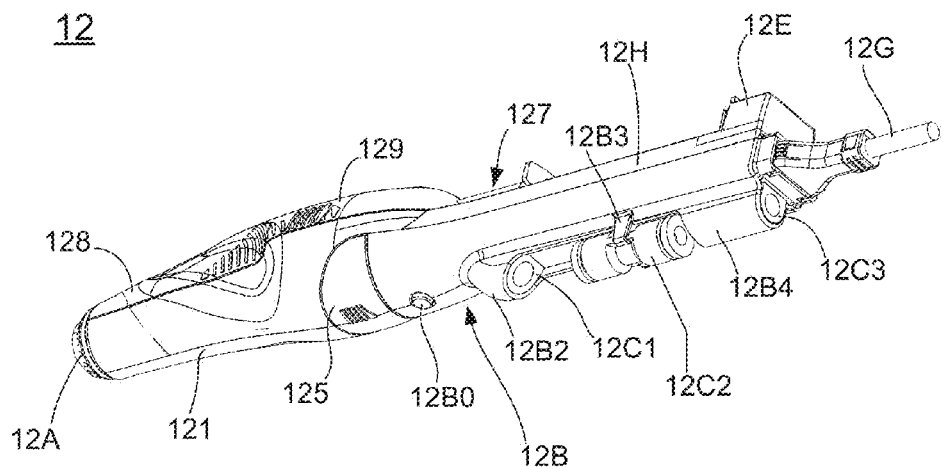
FIGS. 5A and 5B are side views of a needleless drug-injecting device of the needleless liquid medicine injecting system.
Figure 5B:
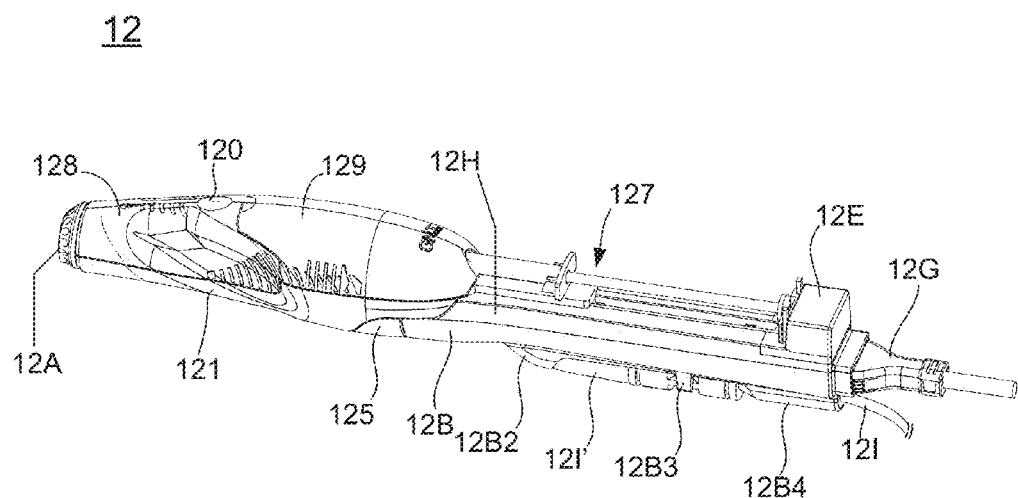
Figure 6:
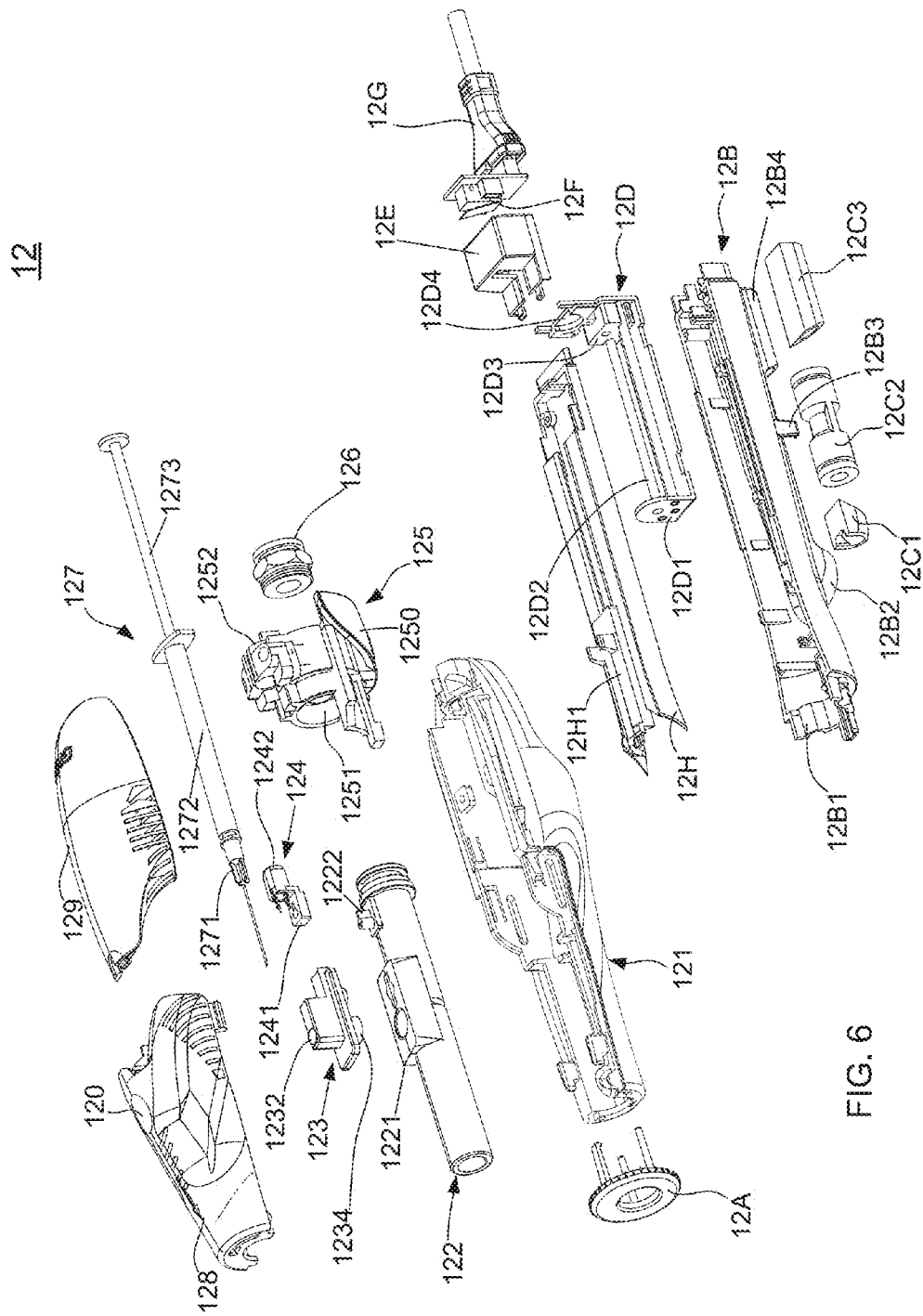
FIG. 6 is an exploded view of the needleless drug-injecting device.

Continuously referring to FIG. 4, and please simultaneously refer to FIG. 5A and FIG. 5B, there are shown side views of the needleless liquid medicine injecting device of the needleless liquid medicine injecting system; moreover, please simultaneously refer to FIG. 6, which illustrate an exploded view of the needleless liquid medicine injecting device. As shown in FIG., the needleless drug-injecting device 12 consists of: a first base 121, a liquid medicine delivering tube 122, a liquid medicine delivery member 123, a needle fixing member 124, a fixed connection base 126, a tube connecting member 127, a sliding cover set, an adjustable nozzle 12A, a second base 12B, a driving module 12D, a controlling circuit module 12F, an accommodating member 12E, and an injection syringe carrying board 12H.

Please refer to FIG. 7A and FIG. 7B, there respectively are shown a top view and a cross-sectional view of the liquid medicine delivering tube, the needle fixing member, the fixed connection base, the tube connecting member, and the injection syringe of the needleless liquid medicine injecting device. As shown in FIG. 6, FIG. 7A and FIG. 7B, the liquid medicine delivering tube 122 is disposed in the first base 121 and respectively formed with an air input end and a liquid medicine output end on the two ends thereof, and the liquid medicine delivery member 123 is disposed on the liquid medicine delivering tube 122 and has an insertion hole 1231. In which, one side of the liquid medicine delivering tube 122 is provided with a delivery member combining portion 1221 and a fixing member combining portion 1222. The needle fixing member 124 includes a first delivery tube combining portion 1241 combined with the fixing member combining portion 1222 on the liquid medicine delivering tube 122 and a fixing portion 1242. In addition, a needle head of the needle 1271 of the injection syringe 127 is inserted into the insertion hole 1231 of the liquid medicine delivery member 123; and opposite, a barrel combining portion of the needle 1271 is fixed in the fixing portion 1242 of the needle fixing member 124.

Besides the insertion hole 1231, the liquid medicine delivery member 123 further includes a pressure relieving hole 1232, an inner tube 1233 and a second delivery tube combining portion 1234, wherein the insertion hole 1231, the inner tube 1233 and the second delivery tube combining portion 1234 are penetrated to each other, and the second delivery tube combining portion 1234 is connected with the delivery tube combining portion 1241. Moreover, the liquid medicine delivering tube 122 is further provided with an auxiliary fixing portion 1221a, and an auxiliary combination portion 1234a is provided on the liquid medicine delivery member 123 opposite to the auxiliary fixing portion 1221a, so as to make the liquid medicine delivery member 123 can be assembled onto the liquid medicine delivering tube 122 easily.

Continuously, the fixed connection base 125 is connected to the rear end of the first base 121 and has bottom plate 1250, a sleeve tube 1251 and a first barrel fixing member 1252, wherein the front of the sleeve tube is disposed on the bottom plate 1250 and connects to the air input end of the liquid medicine delivering tube 122. In addition, the first barrel fixing member 1252 is disposed on the top of the sleeve tube 1251 for fixing the front end of the barrel 1272 of the injection syringe 127. Besides, the tube connecting member 126 is connected with the rear end of the sleeve tube 1251 of the fixed connection base 125.

Moreover, the sliding cover set is assembled with the first base 121 for constituting a housing, so as to accommodate the liquid medicine delivering tube 122, the liquid medicine delivery member 123, the needle fixing member 124, the fixed connection base 125, and the fixed connection base 126. In the present invention, the sliding cover set consists of a front sliding cover 128 and a rear sliding cover 129, such that the liquid medicine delivering tube 122 disposed in the first base 121 can be taken out from the housing after the front sliding cover 128 and the rear sliding cover 129 is opened by sliding. Besides, the top of the sliding cover set is formed with an aperture 120 opposite to the pressure relieving hole 1232 of the liquid medicine delivery member 123. The adjustable nozzle 12A is assembled to a front opening of the housing, wherein a speed-adjusting distance is provided between the adjustable nozzle 12A and the front opening of the housing, and the speed-adjusting distance can be changed by adjusting the distance between the adjustable nozzle 12A and the front opening, so as to modify the speed of the liquid medicine be shot according to the molecular weight of the liquid medicine.

Figure 8:
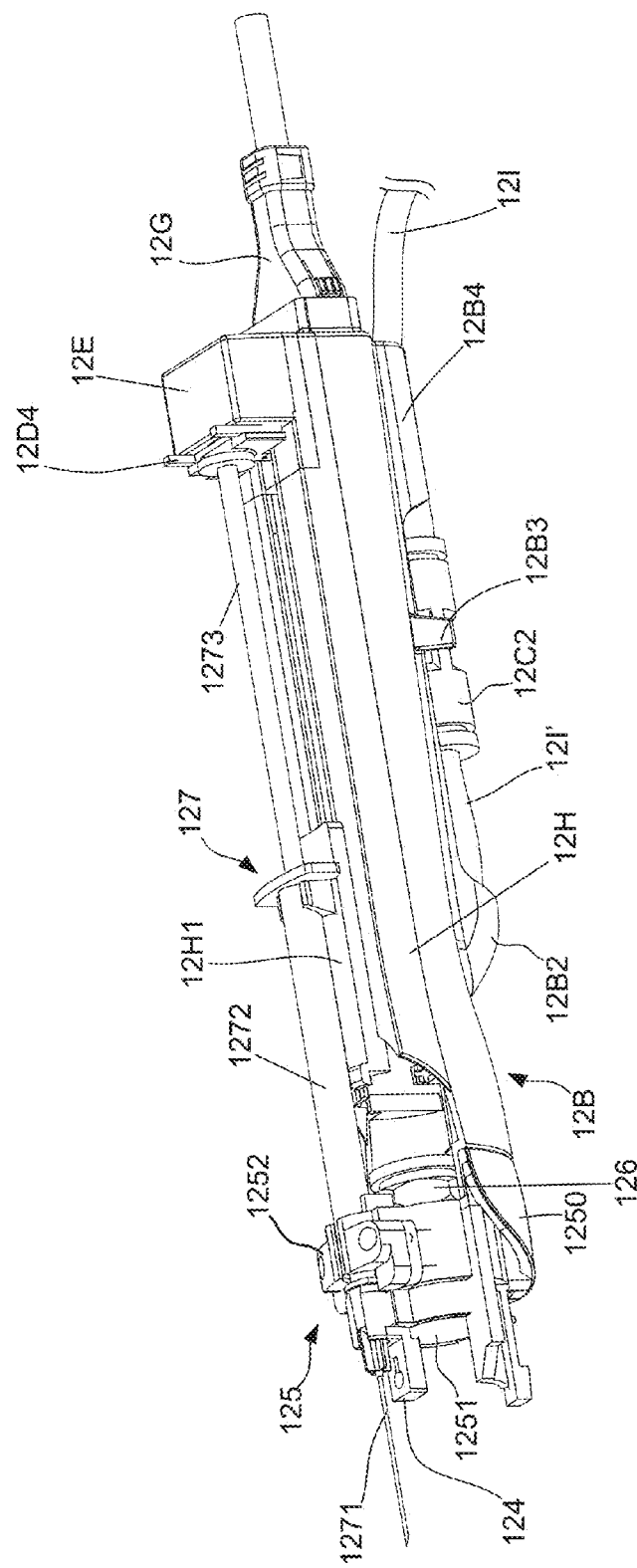
FIG. 8 is a top view of a second base, the fixed connection base, the tube connecting member, the injection syringe, an accommodating member, and an injection syringe carrying board of the needleless drug-injecting device.

Please continuously refer to FIG. 8, which illustrates a top view of the second base, the fixed connection base, the tube connecting member, the injection syringe, an accommodating member, and an injection syringe carrying board of the needleless liquid medicine injecting device. As shown in FIGS., the second base 12B is assembled to the rear end of the first base 121, and disposed with a manual shot-triggering member 12B0, an extended combination member 12B1, a first disposing portion 12B2, a second disposing portion 12B3, and a third disposing portion 12B4. The extended combination member 12B1 is formed on the front end of the second base 12B, and the manual shot-triggering member 12B0 is formed on front end of the bottom of the second base 12B. Moreover, the first disposing portion 12B2 is disposed on the bottom of the second base 12B and adjacent to the manual shot-triggering member 12B0. In addition, the second disposing portion 12B3 is disposed on the bottom of the second base 12B and adjacent to the first disposing portion 12B2; and the third disposing portion 12B4 is disposed on the bottom of the second base 12B and adjacent to the second disposing portion 12B3.

Inheriting to above descriptions, a first tube fixing member 12C1, a fixing member 12C2 and a second tube fixing member 12C3 are disposed in the first disposing portion 12B2, the second disposing portion 12B3 and the third disposing portion 12B4, respectively. Thus, an extended tube can 12I' be connected between the first tube fixing member 12C1 and the fixing member 12C2, and extending into the housing via the first tube fixing member 12C1, so as to be further coupled with the air input end of the liquid medicine delivering tube122 through the tube connecting member 126 and the fixed connection base 125. Besides, the air delivery tube 12I is connected with the fixing member 12C2 through the second tube fixing member 12C3, such that the first air can be delivered into the extended tube 12I' via the fixing member 12C2. Herein, it needs to further explain that, by pressing the manual shot-triggering member 12B0, the residual first air or the residual second air in the extended tube 12I' would be exhausted out through the pressure relieving hole 1232 and the front opening of the housing.

Referring to FIG. 6 again, the driving module 12D is disposed in the second base 12B and consists a framework 12D1, two screw rods 12D2, a sliding block 12D3, a driving motor, wherein the framework 12D1 is disposed in the second base 12B, and the two screw rods are disposed in the framework 12D1. The sliding block 12D3 is disposed on the two screw rods, and respectively provided with one groove on the two sides thereof, wherein the two grooves are used for making the sliding block 12D3 slide on the screw rods 12D2. The driving motor is disposed on the end side of the framework 12D1, used for driving the screw rods 12D2 to rotate according to the control of the controlling circuit module 12F.

Inheriting to above descriptions, the plunger fixing member 12D4 for fixing a pressing portion of the plunger 1273 of the injection syringe 127 is disposed one the sliding block 12D3; therefore, by the control of the controlling circuit module 12F, the driving module 12D would steppedly push the pressing portion of the plunger 1273, and make the liquid medicine stored in the barrel 1272 of the injection syringe 127 be quantitatively injected into the liquid medicine delivery member 123, and then the liquid medicine is delivered into the liquid medicine delivering tube 122 from the liquid medicine delivery member 123.

The accommodating member 12E is disposed on the end side of the framework 12D1 for accommodating the driving motor and the controlling circuit module 12F. The injection syringe carrying board 12H is disposed on the second base 12B for carrying the injection syringe 127, and covering the framework 12D1, the driving motor, the screw rods 12D2, and the sliding block 12D3; moreover, the plunger fixing member 12D4 is exposed out of the injection syringe carrying board 12H, and the rear end of the barrel 1272 of the injection syringe 127 is fixed on a second barrel fixing member 12H1 disposed on the injection syringe carrying board 12H.

Therefore, through above descriptions, the framework and structure of the needleless drug-injecting device 12 have been introduced completely and clearly. Next, the detailed introduction of the controlling device 11 of the needleless drug-injecting system 1 will be carried out in following paragraphs. Referring to FIG. 4 again, and please refer to FIG. 9A, FIG. 9B and FIG. 9C, there are shown side views of the controlling device. As shown in FIGS., the controlling device 11 is electrically connected to the controlling circuit module 12F on the rear end of the needleless drug-injecting device 12 through the electrical cable 12G; moreover, the air delivery tube 121 of the controlling device 11 is connected to the bottom of the rear end of the needleless drug-injecting system device 12 for inputting the air with specific air pressure into the needleless drug-injecting system device 12. In the present invention, the controlling device 11 consists of: a box 111, a first air inputting port 113, an air pressure adjusting valve 112a, an air pressure display module 119, a solenoid valve controlling output port 114, an electrical connection port 115, an operation interface116, a second air inputting port 117, and a heating module 118.

Figure 9A:
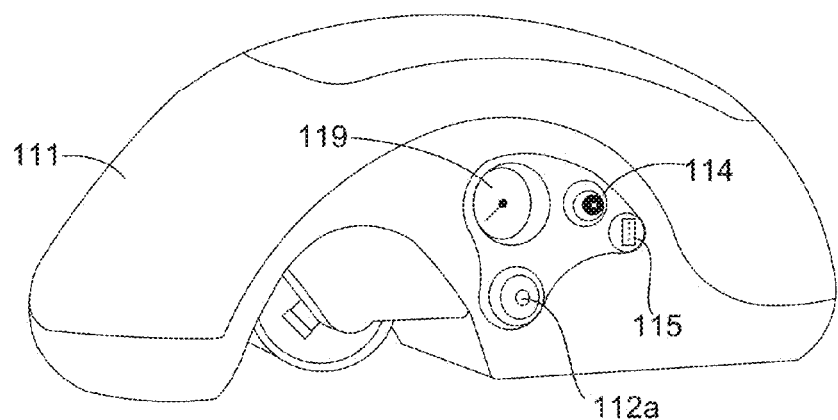

Inheriting to above descriptions, the box 111 is provided with an air pressure modulating module and a controlling and processing model in the internal thereof, moreover, as shown in FIG. 9C, a power switch 112b, a power connector 112c, the first air inputting port 113, and a power outputting interface 112d are disposed on the rear of the box 111. For the box 111, the first air inputting port 113 is used for connecting to an external air source, for example, an air box, such that a first are provided by the air box can be inputted into the air pressure modulating module of the box 111. Particularly, in the present invention, the first air can be nitrogen ($N_2$) or carbon dioxide ($CO_2$). Besides, as shown in FIG. 9A, the air pressure display module 119 is disposed on one side of the box 111 and connected to the air pressure modulating module, used for display the air pressure of the first air modulated by the air pressure modulating module. In addition, the solenoid valve controlling output port 114 is disposed on the one side of the box 111 and connected to the air pressure modulating module, used for outputting the first air having the specific air pressure. The electrical connection port 115 is disposed on one side of the box 111 and coupled to the controlling and processing module; moreover, the electrical connection port 115 is also connected to the electrical cable 12G. The operation interface 116 is disposed on the front side of the box 111, and providing a user to set a plurality of specific parameters, wherein the specific parameters comprises: a usage dose of the liquid medicine, a shot pressure of the liquid medicine, an air flow rate, a single-shot quantity of the liquid medicine, a continuous shot frequency of the liquid medicine, and a continuous shot spacing time.

Figure 9B:
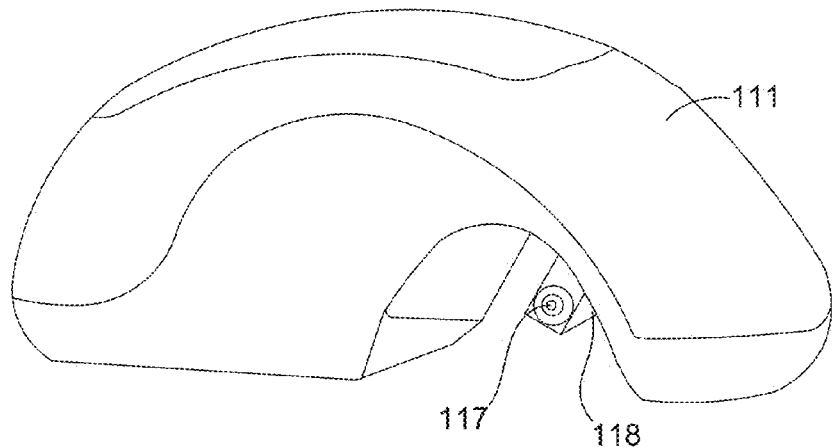

In the controlling device 11, as shown in FIG. 9B, the second air inputting port 117 is disposed on the bottom of the box 111, used for connecting with a portable gas cylinder, so as to facilitate a second air provided by the portable gas cylinder be inputted into the air pressure modulating module of the box 111, wherein the second air is also modulated by the air pressure modulating module for having a specific air pressure. The same to the first air, the second air inputted into the box 111 can be nitrogen ($N_2$) or carbon dioxide ($CO_2$). Furthermore, in order to avoid the second air provided by the gas cylinder from precipitation, the heating module 118 is disposed on the bottom of the box 111 and located between the second air inputting port 117 and the air pressure modulating module, used for heating the second air. Herein, it needs to further explain that, if the user uses the gas cylinder to provide the second air into the box 111, the second air inputted into the box 111 would be modulated by the air pressure modulating module for having a specific air pressure, and outputted through the solenoid valve controlling output port 114.

Figure 10A:
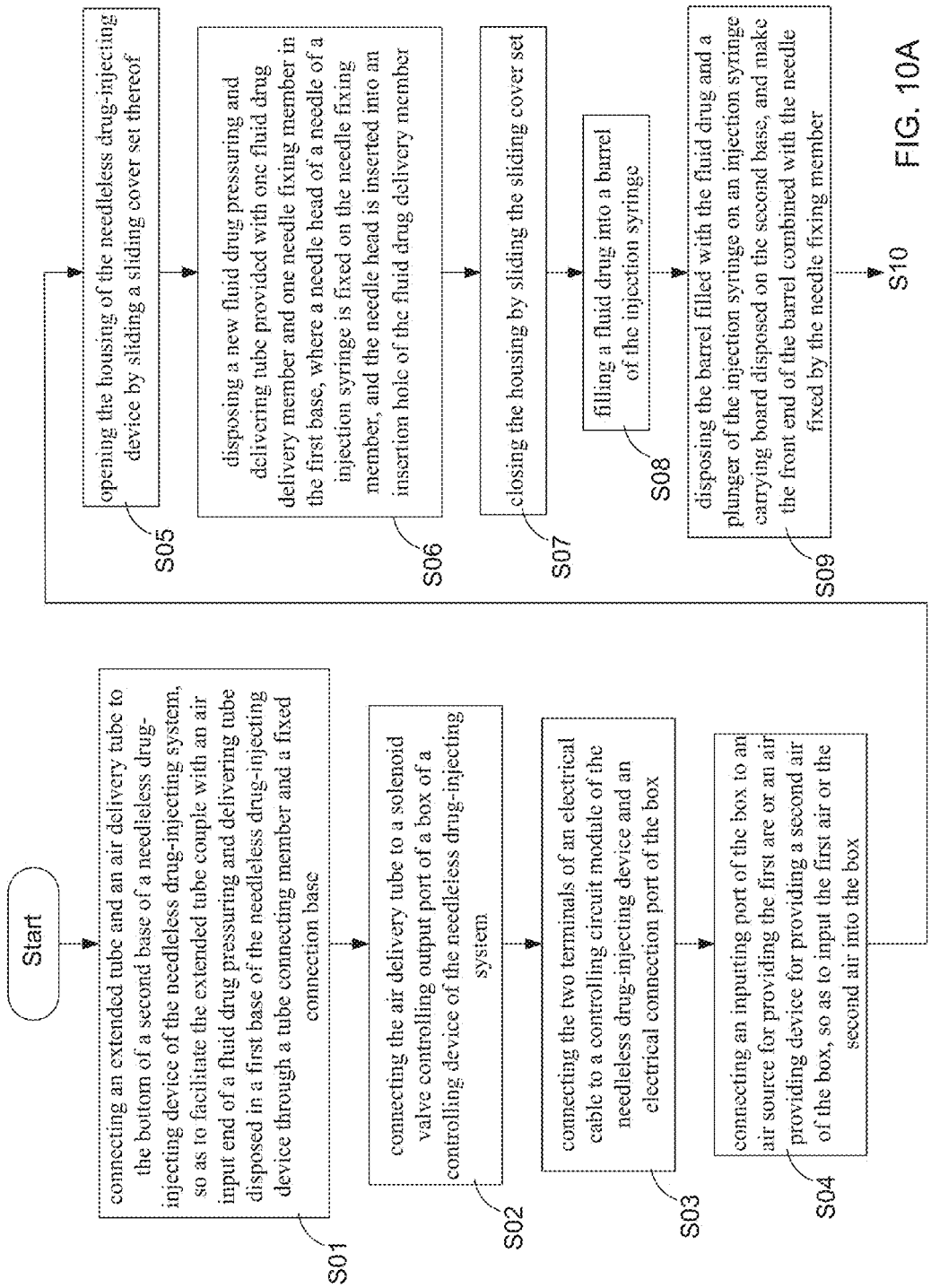
FIGS. 10A and 10B are flow charts of a needleless drug-injecting method according to the present invention.
Figure 10B:
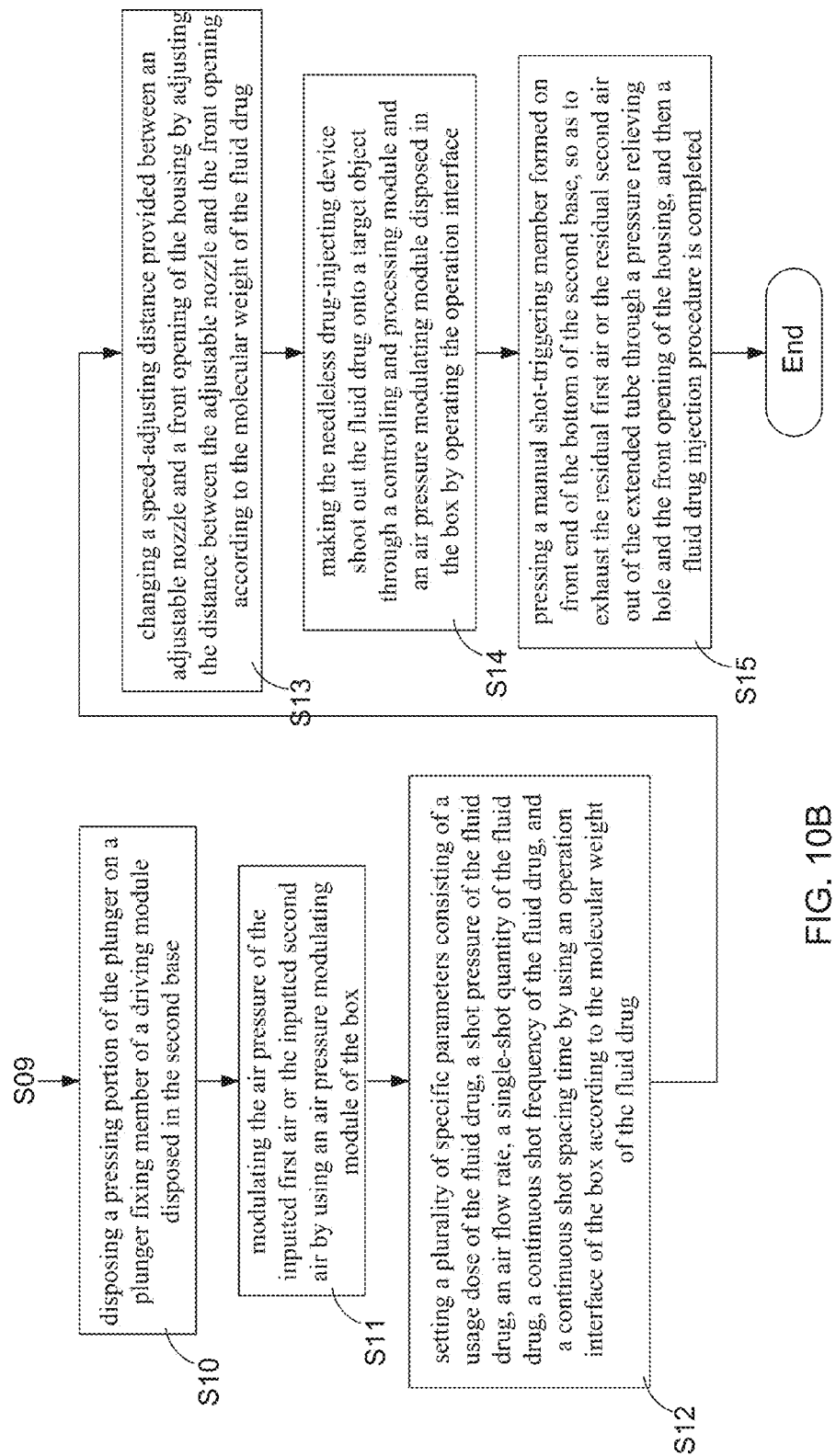

Therefore, through above descriptions, the framework and structure of the needleless drug-injecting system 1 according to the present invention have been introduced completely and clearly. Please refer to FIG. 10A and FIG. 10B, there are shown flow charts of a needleless drug-injecting method according to the present invention; moreover, please simultaneously refer to FIGS. 11A-11N, which depict schematic operation diagrams of the needleless drug-injecting system corresponding to the flow charts. As shown in FIG. 10A, FIG. 11A, FIG. 11B, and FIG. 11C, the needleless drug-injecting method of the present invention firstly proceeds to step (S01) for connecting an extended tube 12I' and an air delivery tube 12I to the bottom of a second base 12B of a needleless drug-injecting device 12, so as to facilitate the extended tube 12I' couple with an air input end of a liquid medicine delivering tube122 disposed in a first base 121 of the needleless drug-injecting device 12 through a tube connecting member 126 and a fixed connection base 125. In which, the aforesaid second base 12B in the step (S01) is provided with a first disposing portion 12B2, a second disposing portion 12B3 and a third disposing portion 12B4 on the bottom thereof, wherein a first tube fixing member 12C1, a fixing member 12C2 and a second tube fixing member 12C3 are disposed in the first tube fixing disposing portion 12B2, the second disposing portion 12B3 and the third disposing portion 12B4, respectively; moreover, the extended tube 12I' is connected between the first tube fixing member 12C1 and the fixing member 12C2, and extending into the housing via the first tube fixing member 121, so as to be further coupled with the air input end of the liquid medicine delivering tube 122 through the tube connecting member 126 and the fixed connection base 125; moreover, the air delivery tube 121 is connected with the fixing member 12C2 through the second tube fixing member 12B3, such that the first air can be delivered into the extended tube 12I' via the fixing member 12C2.

Continuously, step (S02) is executed for connecting the air delivery tube 121 to a solenoid valve controlling output port 114 of a box 111 of a controlling device 11 of the needleless drug-injecting system 1; then, step (S03) is executed for connecting the two terminals of an electrical cable 12G to a controlling circuit module 12F of the needleless drug-injecting device 12 and an electrical connection port 115 of the box 11. Subsequently, the method proceeds to step (S04) for connecting an inputting port of the box 111 to an air source for providing the first are or an air providing device for providing a second air of the box, so as to input the first air or the second air into the box 111. In which, the aforesaid air source in the step (S04) is an air box, and the inputting port connected to the air box is the first air inputting port 113, wherein the first air provided by the air box can be nitrogen ($N_2$) or carbon dioxide ($CO_2$).

Inheriting to above descriptions, moreover, the aforesaid air providing device in the step (S04) is a portable gas cylinder, and the inputting port connected to the air box would be the second air inputting port 117, wherein the second air provided by the gas cylinder can be nitrogen ($N_2$) or carbon dioxide ($CO_2$). Furthermore, in order to avoid the second air provided by the gas cylinder from precipitation, the heating module 118 is disposed on the bottom of the box 111 and located between the second air inputting port 117 and the air pressure modulating module, used for heating the second air. As shown in FIG. 9B and FIG. 9C, the necessary power of the heating module 118 is provide by the power outputting interface 112d disposed on the rear of the box 111.

Figure 11A:
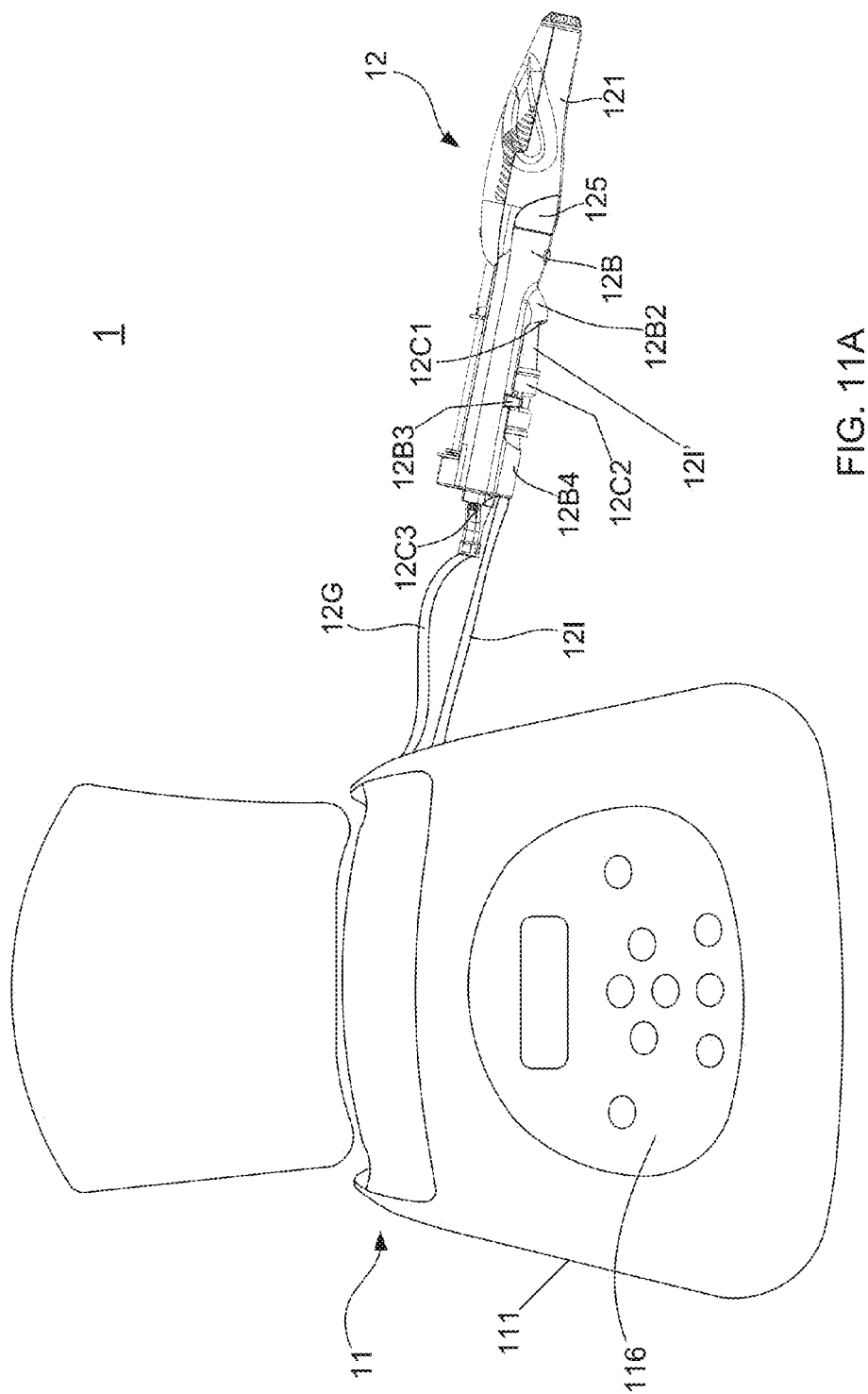
FIGS. 11A-11N are schematic operation diagrams of the needleless drug-injecting system.
Figure 11B:
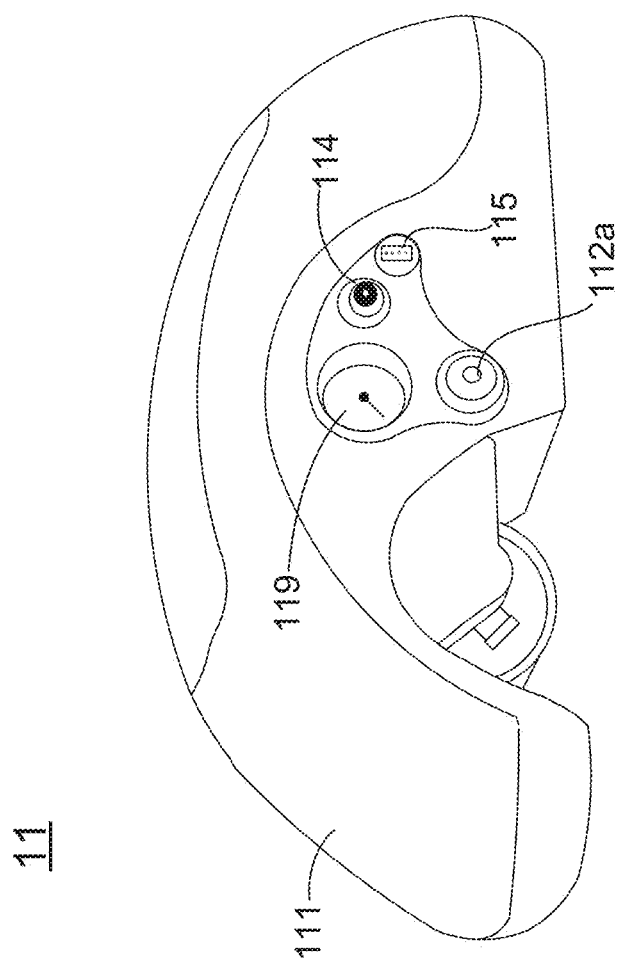
Figure 11D:
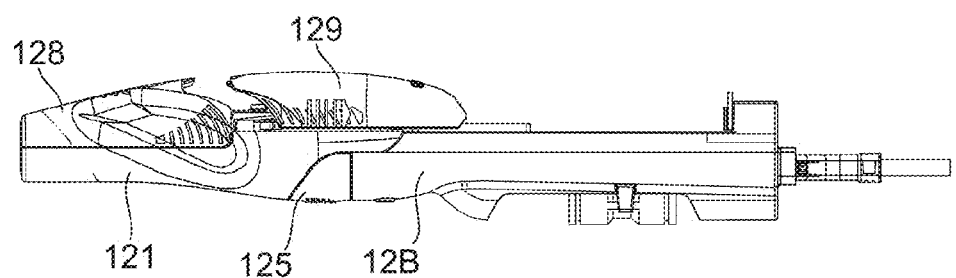
Figure 11E:
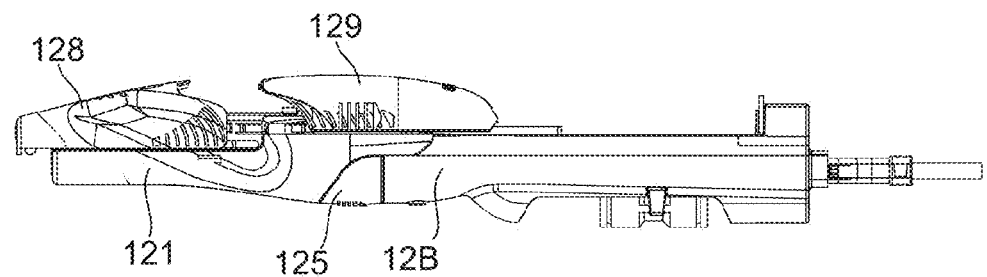
Figure 11F:
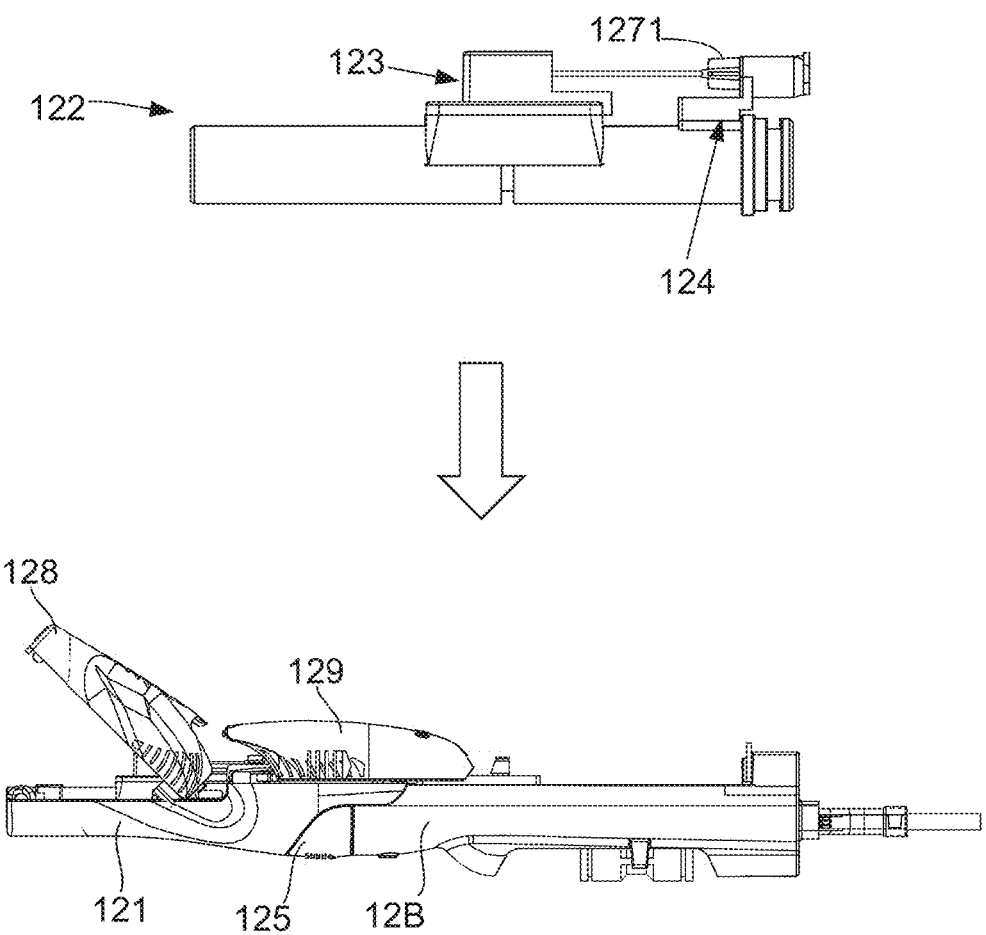

After the connection of the controlling device 11, the needleless drug-injecting device 12 and the air source, the method continuously proceeds to step (S05) for opening the housing of the needleless drug-injecting device 12 by sliding the sliding cover set thereof. As shown in FIG. 11D and FIG. 11E, it needs to firstly execute steps (S051) and (S052) for backward sliding a rear sliding cover 129 and forward sliding a front sliding cover 128, so as to open the sliding cover set from the housing.

Figure 11G:
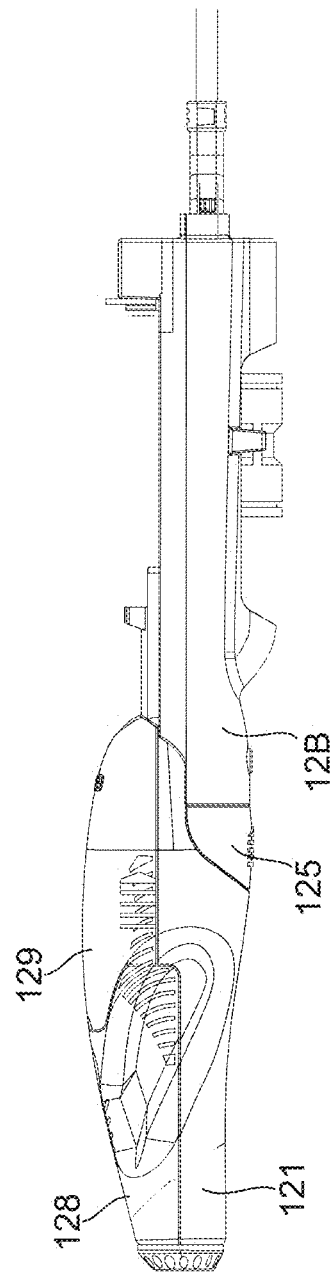

Continuously, the method proceeds to step (S06) disposing a new liquid medicine delivering tube 122 provided with one liquid medicine delivery member 123 and one needle fixing member 124 in the first base 121. As shown in FIG. 11F, FIG. 6, FIG. 7A, and FIG. 7B, a needle head of a needle 1271 of a injection syringe 127 is fixed on the needle fixing member 124, and the needle head is inserted into an insertion hole 1231 of the liquid medicine delivery member 123. Next, step (S07) is executed for closing the housing by sliding the sliding cover set, in which step (S07) is completed by executed steps (S071) and (S072) in turns, so as to make the front sliding cover down and the rear slide cover slide backward, and then make the rear sliding cover forward slide; therefore, as shown in FIG. 11G, the housing is closed.

Figure 11H:
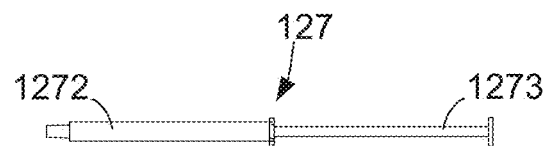
Figure 11I:
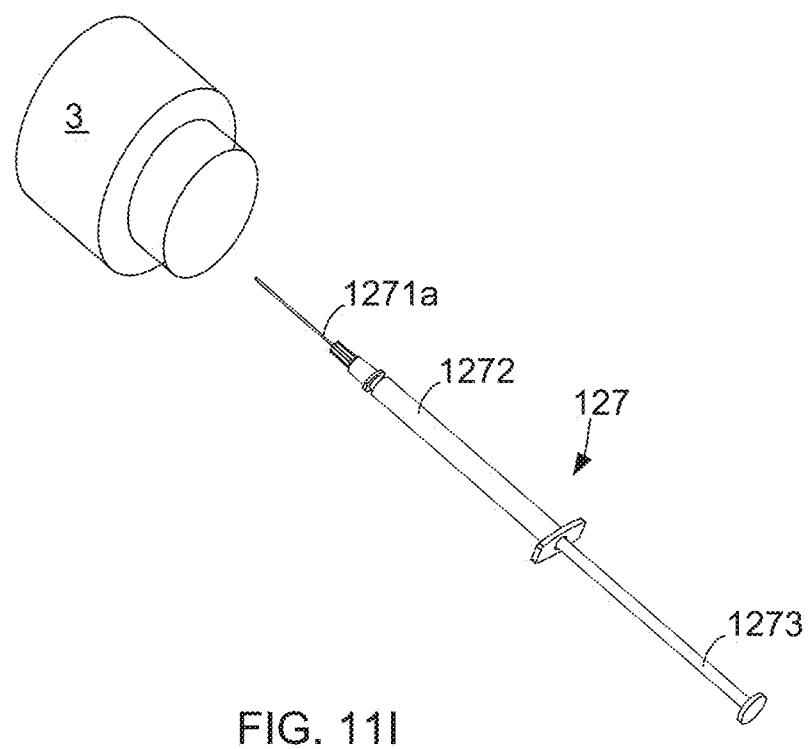

Subsequently the method proceeds to step (S08) for filling a liquid medicine into a barrel 1272 of the injection syringe 127. As shown in FIG. 11H and FIG. 11I, to complete the step (S08), it needs to firstly execute steps (S081) and (S082) for taking the barrel 1272 and the plunger 1273 of the injection syringe 127 and assembling an external needle 1271a to the barrel 1272. Next, to execute step (S083) for filling the liquid medicine accommodated in a liquid medicine accommodating device 3 into the barrel 1272 by using the plunger 1273 and the external needle 1271a; therefore, after the step (S083) is finished, step (S084) is eventually be executed for removing the external needle 1271a from the barrel 1272.

Figure 11J:
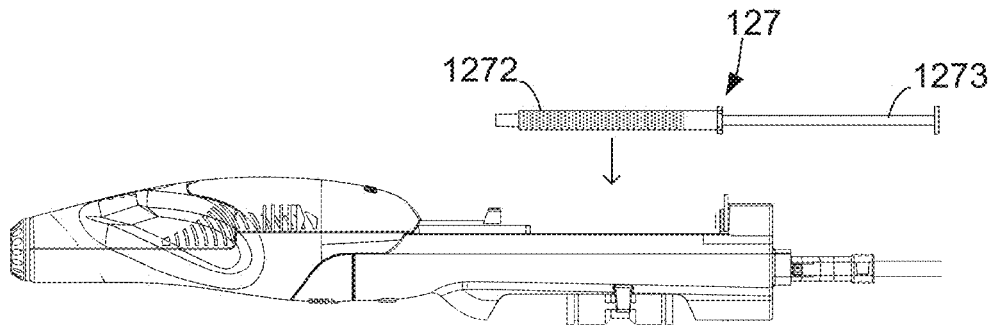
Figure 11K:
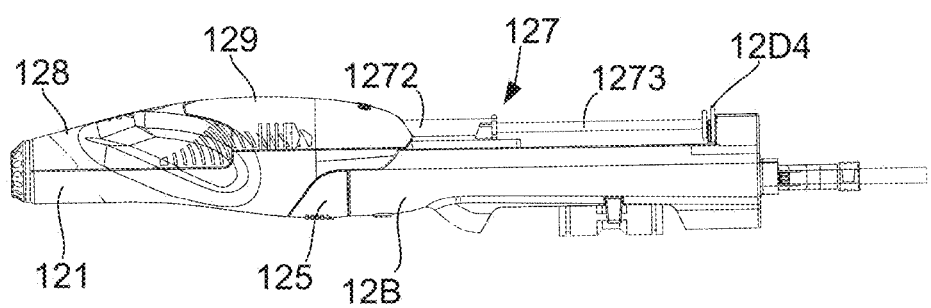

As shown in FIG. 11J and FIG. 11K, the method continuously proceeds to step (S09) for disposing the barrel 1272 filled with the liquid medicine and the plunger 1273 of the injection syringe 127 on an injection syringe carrying board 12H disposed on the second base 12B, and make the front end of the barrel 1272 combined with the needle 1271 fixed by the needle fixing member 124; and next proceeding to step (S10) for disposing a pressing portion of the plunger 1273 on a plunger fixing member 12D4 of a driving module 12D disposed in the second base 12B.

After the step (S10) is completed, the method subsequently proceeds to step (S11) for modulating the air pressure of the inputted first air or the inputted second air by using an air pressure modulating module of the box 111; and next proceeding to step (S12) for setting a plurality of specific parameters consisting of a usage dose of the liquid medicine, a shot pressure of the liquid medicine, an air flow rate, a single-shot quantity of the liquid medicine, a continuous shot frequency of the liquid medicine, and a continuous shot spacing time by using an operation interface 116 of the box 111 according to the molecular weight of the liquid medicine. In the present invention, the molecular weight of the liquid medicine is less than 80 kDa, and the composition of the liquid medicine can be DNA, RNA, DNA enclosed by nano-gold, RNA enclosed by nano-gold, vaccination, collagen, or hyaluronic acid. Moreover, for above-mentioned parameters, the shot pressure of the liquid medicine is ranged from 50 psi to 300 psi, the single-shot quantity of the liquid medicine is raged from 1 µl to 100 µl.

Figure 11M:

Continuously, the method proceeds to step (S13) for changing a speed-adjusting distance provided between an adjustable nozzle 12A and a front opening of the housing by adjusting the distance between the adjustable nozzle 12A and the front opening according to the molecular weight of the liquid medicine. Generally, the greater the molecular weight of the liquid medicine is, the longer the speed-adjusting distance is, and vice versa. Subsequently, the method proceeds to step (S014) for making the needleless drug-injecting device 12 shoot out the liquid medicine onto a target object through a controlling and processing module and an air pressure modulating module disposed in the box 111 by operating the operation interface 116; as shown in FIG. 11M, shooting out the liquid medicine onto a human face.

Figure 11N:
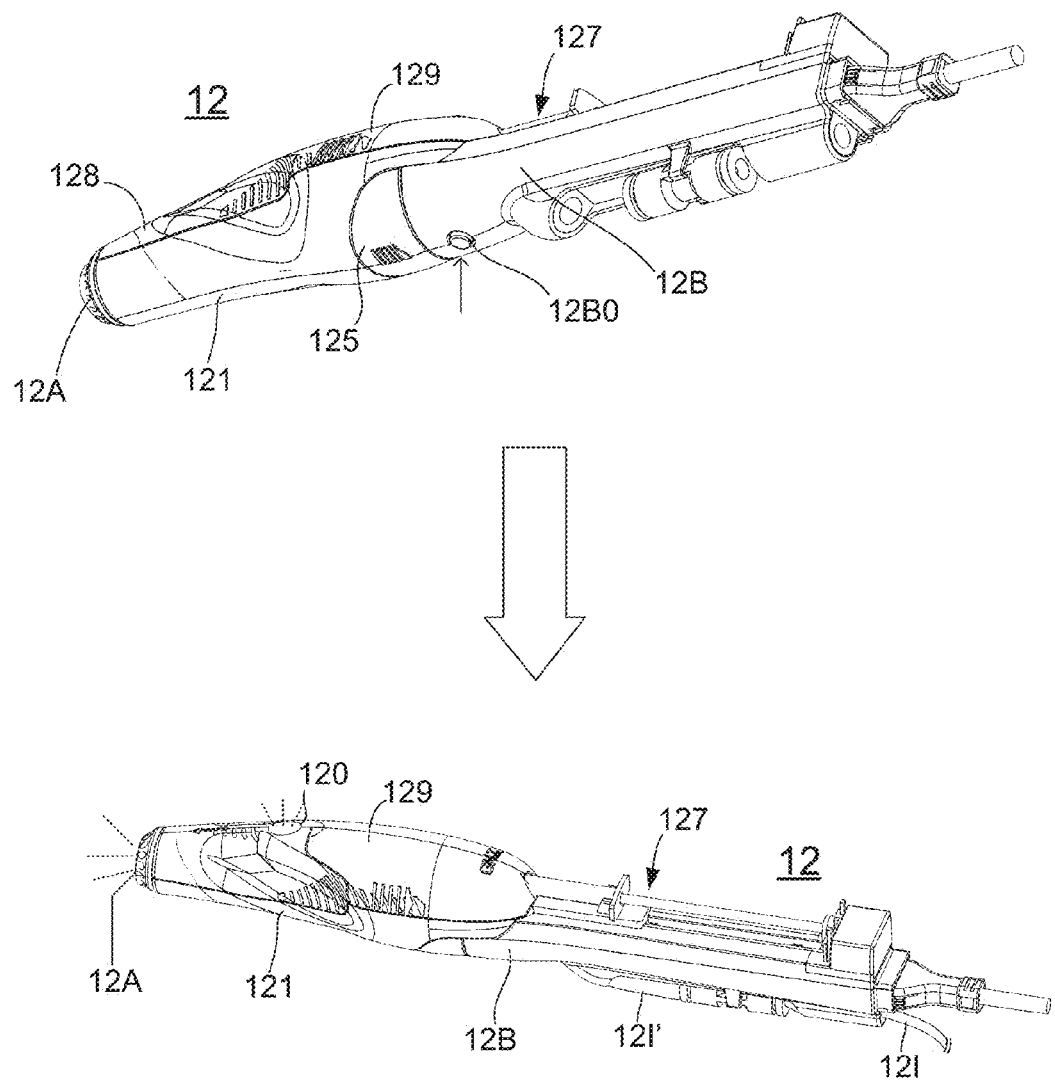

As shown in FIG. 11N, eventually, the method proceeds to step (S15) for closing the air source and then pressing a manual shot-triggering member 12B0 formed on front end of the bottom of the second base 12B, so as to exhaust the residual first air or the residual second air out of the extended tube 121' through a pressure relieving hole 1232 and the front opening of the housing, and then a liquid medicine injection procedure is completed.

Thus, through above descriptions, the needleless drug-injecting system and the method thereof according to the present invention have been introduce completely and clearly; next, for improving the efficiency of the needleless drug-injecting system and the method, a variety of experiment data are presented in follows. With reference to FIG. 12, there is shown slice images of rat skin tissues. Wherein, image (a) shows the skin tissue of a control rat, which does not be injected with a nano-gold composition. Image (b) also shows the skin tissue of a control rat, but this control rat is injected with a phosphate buffered solution (PBS). Opposite to images (a) and (b), the images (c), (d) and (e) of FIG. 12 show the skin tissues of different experiment rats, in which the experiment rats are injected with the nano-gold compositions with the size of 1-3 nm, 3-5 nm and 30 nm, respectively. Herein, it needs to further explain that, the injection conditions for the control rat of image (b) and the experiment rats of images (c), (d) and (e) are as follows: 100 psi shot pressure and 50 µl single-shot quantity. The most important is that, as shown in FIG. 12, not only the skin tissue of the control rat does not reveal any inflammation, but also all of the experiment rats' skin tissue does not reveal any inflammation. So that, the experiment results of FIG. 12 prove that the needleless drug-injecting system and the method thereof proposed by the present invention would not cause any hurt on rat skin.

Figure 13:
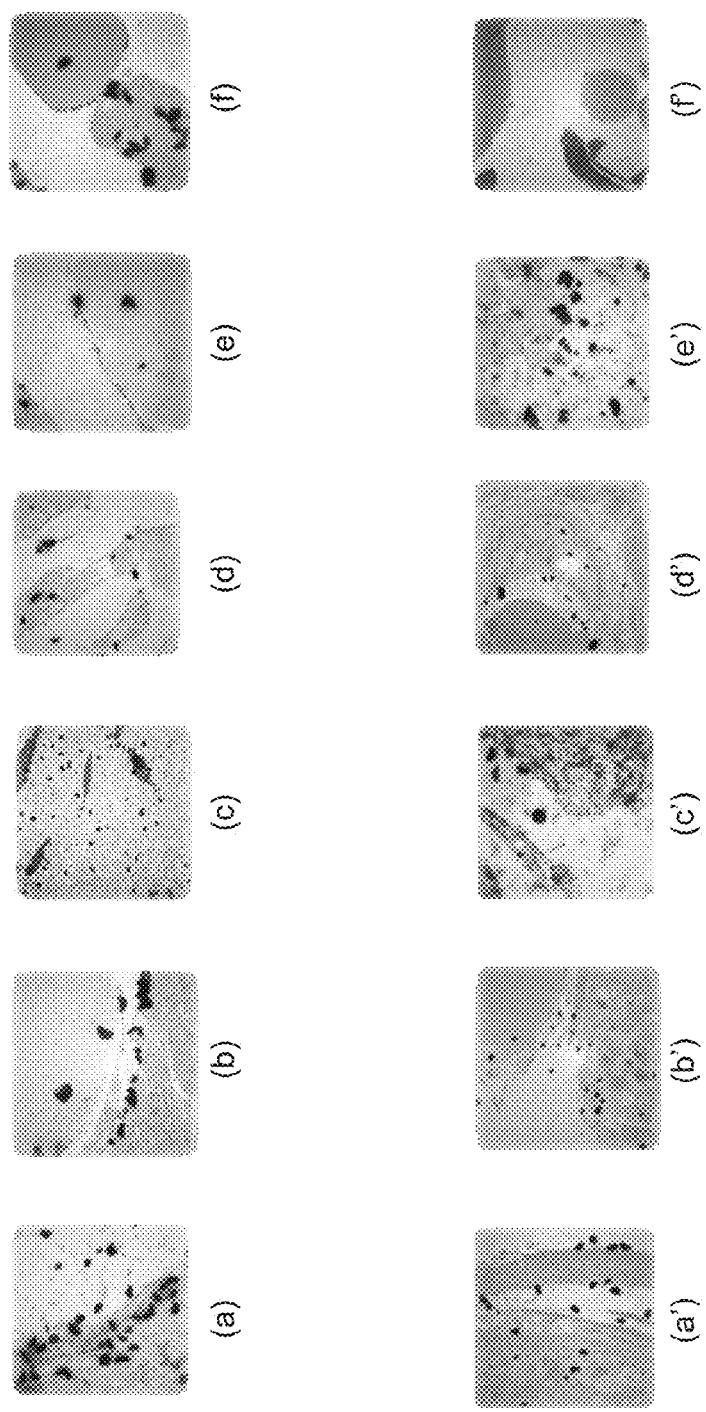
FIG. 13 is slice images of rat skin tissues after being injected with nano gold.

Please refer to FIG. 13, there are shown slice images of rat skin tissues after being injected with nano-gold, wherein images (a), (b), (c), (d), (e), and (f) respectively show the skin tissue of different rats injected with the nano-gold compositions having the size of 600 nm, 400 nm, 300 nm, 100 nm, 30 nm, and 1-3 nm by using 150 psi shot pressure. Oppositely, images (a'), (b'), (c'), (d'), (e'), and (f') respectively show the skin tissue of different rats injected with the nano-gold compositions having the size of 600 nm, 400 nm, 300 nm, 100 nm, 30 nm, and 1-3 nm by using 100 psi shot pressure. Therefore, the experiment results of FIG. 13 prove that the nano-gold compositions with the same size can be injected into rat skin under different shot pressure (150 psi or 100 psi) by using the needleless drug-injecting system 1 proposed by the present invention.

Thus, through above descriptions, the needleless drug-injecting system and the method thereof according to the present invention have been introduce completely and clearly, moreover, the efficiency of the needleless drug-injecting system and the method thereof does also be proven by various experiment data; in summary, the present invention includes the advantages of:

(1) The needleless drug-injecting system 1 of the present invention provides the user for individually set a variety of parameters comprising usage dose of liquid medicine, shot pressure of liquid medicine, air flow rate, single-shot quantity of liquid medicine, continuous shot frequency of liquid medicine, and a continuous shot spacing time according to different liquid medicine.

(2) Inheriting to above point 1, Thus, after setting the parameters, the liquid medicine can be injected into the dermis layer of the face skin of a human when the user using this needleless drug-injecting system 1 to inject any one liquid medicine to the human face, therefore the liquid medicine would be absorbed by the face skin without hurting the human face.

(3) Moreover, by using this needleless drug-injecting system 1, the user is able to selectively inject the liquid medicine to the human face by one single shot or multi continuous shot, and such way can effectively make all of the various liquid medicine be injected into the human face completely.

The above description is made on embodiments of the present invention. However, the embodiments are not intended to limit scope of the present invention, and all equivalent implementations or alterations within the spirit of the present invention still fall within the scope of the present invention.

What is claimed is:

1. A needleless drug-injecting system, comprising:
 a needleless drug-injecting device, comprising:
  a liquid medicine delivering tube, being disposed in the first base and respectively formed with an air input end and a liquid medicine output end on the two ends thereof, wherein one side of the liquid medicine delivering tube is provided with an delivery member combining portion;
  a liquid medicine delivery member, being disposed on the liquid medicine delivering tube and having an insertion hole and a pressure relieving hole;
  a fixed connection base, being connected to the rear end of the first base and having a sleeve tube, wherein the front of the sleeve tube is connected to the air input end of the liquid medicine delivering tube;
  a tube connecting member, being connected with the rear end of the sleeve tube of the fixed connection base;
  an injection syringe, having a needle, a barrel and a plunger, wherein the needle of the injection syringe is inserted into the insertion hole of the liquid medicine delivery member;
  a sliding cover set, being assembled with the first base for constituting a housing, wherein the liquid medicine delivering tube, the liquid medicine delivery member, and the fixed connection base are accommodated by the housing;
  an adjustable nozzle, being assembled to a front opening of the housing, wherein a speed-adjusting distance is provided between the adjustable nozzle and the front opening of the housing, and the speed-adjusting distance can be changed by adjusting the distance between the adjustable nozzle and the front opening, so as to modify the speed of a liquid medicine be shot according to the molecular weight of the liquid medicine;

a second base, being assembled to the rear end of the first base, and an extension tube and an air delivery tube being connected to the bottom of the second base, wherein the extension tube is further coupled to the air input end of the liquid medicine delivering tube through the tube connecting member and the fixed connection base in the housing; and a driving module, being disposed in the second base and having a plunger fixing member for fixing a pressing portion of the plunger, wherein the driving module is controlled by a controlling circuit module, so as to steppedly push the pressing portion and make the liquid medicine stored in the barrel of the injection syringe be quantitatively injected into the liquid medicine delivery member, and then the liquid medicine is delivered into the liquid medicine delivering tube from the liquid medicine delivery member; and a controlling device, being electrically connected to the controlling circuit module of the needleless drug-injecting device through an electrical cable thereof, and comprising:

a box, being provided with an air pressure modulating module and a controlling and processing model in the internal thereof;

a first air inputting port, being disposed on one side of the box, and used for connecting an external air source, wherein a first air provided by the air source is inputted into the air pressure modulating module through the first air inputting port;

an air pressure adjusting valve, being used for modulating the air pressure of the first air;

a solenoid valve controlling output port, being disposed on the one side of the box and connected to the air pressure modulating module, used for outputting the first air having a specific air pressure;

an electrical connection port, being disposed on one side of the box and coupled to the controlling and processing module, moreover, the electrical connection port being also connected to the electrical cable; and an operation interface, being disposed on the front side of the box, and providing a user to set a plurality of specific parameters, wherein the specific parameters comprises: a usage dose of the liquid medicine, a shot pressure of the liquid medicine, an air flow rate, a single-shot quantity of the liquid medicine, a continuous shot frequency of the liquid medicine, and a continuous shot spacing time.

2. The needleless drug-injecting system of claim 1, wherein a fixing member combining portion is further disposed on the liquid medicine delivering tube.

3. The needleless drug-injecting system of claim 2, wherein the needleless drug-injecting further comprises: a needle fixing member, having a first delivery tube combining portion combined with the fixing member combining portion on the liquid medicine delivering tube and a fixing portion, wherein a needle head of the needle of the injection syringe is inserted into the insertion hole of the liquid medicine delivery member, and the a barrel combining portion of the needle is fixed in the fixing portion of the needle fixing member.

4. The needleless drug-injecting system of claim 3, wherein the liquid medicine delivery member further comprises an inner tube and a second delivery tube combining portion, wherein the insertion hole, the inner tube and the second delivery tube combining portion are penetrated to each other, and the second delivery tube combining portion is connected with the delivery tube combining portion.

5. The needleless drug-injecting system of claim 1, wherein the fixed connection base further comprises a bottom plate and a first barrel fixing member, in which the first barrel fixing member is disposed on the top over sleeve tube for fixing the front end of the barrel of the injection syringe.

6. The needleless drug-injecting system of claim 5, wherein the driving module further comprises:

a framework, being disposed in the second base;

at least one screw rod, being disposed in the framework;

a sliding block, being disposed on the screw rod, and respectively provided with one groove on the two sides thereof, used for making the sliding block slide on the screw rod; and a driving motor, being disposed on the end side of the framework, used for driving the screw rod to rotate according to the control of the controlling circuit module.

7. The needleless drug-injecting system of claim 6, further comprising:

an accommodating member, being deposed on the end side of the framework for accommodating the driving motor and the controlling circuit module; and an injection syringe carrying board, being disposed on the second base for carrying the injection syringe, and covering the framework, the driving motor, the screw rod, and the sliding block; moreover, the plunger fixing member is exposed out of the injection syringe carrying board, and the rear end of the barrel of the injection syringe is fixed on a second barrel fixing member disposed on the injection syringe carrying board.

8. The needleless drug-injecting system of claim 1, wherein the sliding cover set comprises a front sliding cover and a rear sliding cover, and the housing can be opened by sliding the front sliding cover and the rear sliding cover, so as to take out the liquid medicine delivering tube disposed in the first base from the housing.

9. The needleless drug-injecting system of claim 1, wherein the second base further comprises:

an extended combination member, being formed on the front end of the second base;

a manual shot-triggering member, being formed on front end of the bottom of the second base;

a first disposing portion, being disposed on the bottom of the second base and adjacent to the manual shot-triggering member;

a second disposing portion, being disposed on the bottom of the second base and adjacent to the first disposing portion; and a third disposing portion, being disposed on the bottom of the second base and adjacent to the second disposing portion;

wherein a first tube fixing member, a fixing member and a second tube fixing member are disposed in the first disposing portion, the second disposing portion and the third disposing portion, respectively; moreover, an extended tube being connected between the first tube fixing member and the fixing member, and extending into the housing via the first tube fixing member, so as to be further coupled with the air input end of the liquid medicine delivering tube through the tube connecting member and the fixed connection base;

wherein the air delivery tube is connected with the fixing member through the second tube fixing member, such that the first air can be delivered into the extended tube via the fixing member.

10. The needleless drug-injecting system of claim 1, wherein the controlling device further comprises:
  a second air inputting port, being disposed on the bottom of the box, used for connecting with a portable gas cylinder, so as to facilitate a second air provided by the portable gas cylinder be inputted into the air pressure modulating module;
  a heating module, being disposed on the bottom of the box and located between the air inputting interface and air pressure modulating module, used for heating the second air; and
  an air pressure display module, being disposed on one side of the box and connected to the air pressure modulating module, used for display the air pressure of the first air and the second air modulated by the air pressure modulating module.

11. The needleless drug-injecting system of claim 10, wherein the top of the sliding cover set is provided with an aperture opposite to the pressure relieving hole of the liquid medicine delivery member; moreover, by pressing the manual shot-triggering member, the residual first air or the residual second air in the extended tube would be exhausted out through the pressure relieving hole and the front opening of the housing.

12. The needleless drug-injecting system of claim 1, wherein the composition of the liquid medicine is selected from the group consisting of: DNA, RNA, DNA enclosed by nano-gold, RNA enclosed by nano-gold, vaccination, collagen, and hyaluronic acid.

13. The needleless drug-injecting system of claim 1, wherein the molecular weight of the liquid medicine is less than 80 kDa, the shot pressure of the liquid medicine being ranged from 50 psi to 300 psi, the single-shot quantity of the liquid medicine being ranged from 1 µl to 100 µl.

* * * * *